United States Patent
Kawabata et al.

(10) Patent No.: US 9,495,736 B2
(45) Date of Patent: *Nov. 15, 2016

(54) IMAGE INSPECTING APPARATUS AND IMAGE INSPECTING PROGRAM

(71) Applicant: PROSPER CREATIVE CO., LTD., Tokyo-to (JP)

(72) Inventors: Hideki Kawabata, Tokyo (JP); Akira Kijima, Tokyo (JP)

(73) Assignee: PROSPER CREATIVE CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/373,921

(22) PCT Filed: Feb. 3, 2014

(86) PCT No.: PCT/JP2014/052448
§ 371 (c)(1),
(2) Date: Jul. 23, 2014

(87) PCT Pub. No.: WO2015/114833
PCT Pub. Date: Aug. 6, 2015

(65) Prior Publication Data
US 2015/0220809 A1    Aug. 6, 2015

(51) Int. Cl.
*G06T 7/00* (2006.01)
*H04N 1/00* (2006.01)
(Continued)

(52) U.S. Cl.
CPC ....... *G06T 7/0002* (2013.01); *G06F 17/30247* (2013.01); *G06K 9/00483* (2013.01);
(Continued)

(58) Field of Classification Search
None
See application file for complete search history.

(56) References Cited

U.S. PATENT DOCUMENTS

| 7,162,073 B1 | 1/2007 | Akgul et al. |
| 2001/0033683 A1 | 10/2001 | Tanaka et al. |

(Continued)

FOREIGN PATENT DOCUMENTS

| JP | H11-234500 A | 8/1999 |
| JP | A-2001-304842 | 10/2001 |

(Continued)

OTHER PUBLICATIONS

Written Opinion of the International Searching Authority issued in International Application No. PCT/JP2014/052448 mailed on Apr. 15, 2014.

(Continued)

*Primary Examiner* — Kim Vu
*Assistant Examiner* — Nathan Bloom
(74) *Attorney, Agent, or Firm* — Oliff PLC

(57) ABSTRACT

Image inspecting apparatus compares first image data created as data representing a reference-image acting as an inspecting reference with second image data created as data representing an inspection-image acting as a target to automatically extract a difference point between first and second image data, and includes a storage means for the reference- and inspection-image, an image processing means for establishing correspondences between part of stored reference-image as first image data with part of stored target image as second image data at a pixel level to perform an image matching processing of them, a difference detecting means for comparing image-matched first and second image data to detect a difference between first and second image data, image producing means for comparing difference with a plurality of threshold values to produce error representing image data at each threshold value, and inspecting process using produced error representing image data at each threshold value.

23 Claims, 17 Drawing Sheets

(51) Int. Cl.
G06K 9/00 (2006.01)
G06F 17/30 (2006.01)
G06T 7/40 (2006.01)
G01N 21/956 (2006.01)

(52) U.S. Cl.
CPC ............... *G06T 7/001* (2013.01); *G06T 7/003* (2013.01); *G06T 7/0024* (2013.01); *G06T 7/408* (2013.01); *H04N 1/00015* (2013.01); *G01N 2021/95615* (2013.01); *G06T 2207/10024* (2013.01); *G06T 2207/20021* (2013.01); *G06T 2207/30144* (2013.01); *G06T 2207/30176* (2013.01)

(56) References Cited

U.S. PATENT DOCUMENTS

| | | | |
|---|---|---|---|
| 2002/0051565 | A1 | 5/2002 | Hiroi et al. |
| 2003/0007677 | A1 | 1/2003 | Hiroi et al. |
| 2003/0222976 | A1* | 12/2003 | Duran .............................. 348/43 |
| 2004/0012775 | A1* | 1/2004 | Kinney ....................... 356/237.2 |
| 2005/0008217 | A1 | 1/2005 | Luu et al. |
| 2008/0163140 | A1 | 7/2008 | Fouquet et al. |
| 2011/0040660 | A1* | 2/2011 | Allison ................ G06Q 10/087 705/28 |
| 2011/0293146 | A1* | 12/2011 | Grycewicz .................... 382/106 |
| 2012/0045115 | A1 | 2/2012 | Dong et al. |
| 2013/0044342 | A1 | 2/2013 | Kaneko et al. |
| 2013/0058558 | A1* | 3/2013 | Ueno ........................... 382/144 |
| 2014/0139883 | A1* | 5/2014 | Hashizume ................. 358/3.06 |

FOREIGN PATENT DOCUMENTS

| | | |
|---|---|---|
| JP | 2009-272834 A | 11/2009 |
| JP | A-2013-80524 | 5/2013 |
| JP | A-2013-120170 | 6/2013 |

OTHER PUBLICATIONS

Feb. 9, 2015 Partial European Search Report issued in European Application No. 14 17 8974.3.
Jun. 2, 2015 Extended Search Report issued in European Patent Application No. 14178974.3.
International Search Report issued in International Patent Application No. PCT/JP2014/052448 mailed on Apr. 15, 2014 (with translation).
Jul. 17, 2015 Office Action issued in U.S. Appl. No. 14/338,690.
May 20, 2016 Office Action Issued in U.S. Appl. No. 14/338,690.

* cited by examiner

FIG. 16

Inspection evaluation report :

Objects to be compared (two selection) : ☑PDF(TIFF) ☐Sample ☐Proof ☐OK sheet ☑Normal printing
Date: October 25, 2013
Division: ☐DTP ☐Prepress ☐Printing ☑Quality management ☐Business
Person in charge: Tarou Yamada
Job name: PROS0093
Trade name: New product pamphlet
Detail matter: Catalogue 16 pages (1 folding)
Inspection result: NG            Color evaluation:         OK
Inspector confirmation: Confirmation, Yes or No ☑   Evaluation:  OK ☑   NG ☐
Client confirmation: Confirmation, Yes or No ☐    Evaluation:  OK ☐   NG ☐

Inspection result:

| No. | Character/Inspection | Color/Inspection | Number of errors/Confirmation | Threshold value: Density/Color |
|---|---|---|---|---|
| 1. | 0/0 OK | 0/0 OK | 0 OK | 0/5 |
| 2. | 3/0 NG | 0/0 OK | 0 NG | 5/10 |
| 3. | 2/1 NG | 1/1 OK | 1 NG | 10/10 |
| 4. | 2/2 NG | 2/2 OK | 2 NG | 10/10 |
| 5. | | | | |
| 6. | | | | |
| 7. | | | | |
| 8. | | | | |
| 9. | | | | |
| 10. | | | | |
| 11. | | | | |
| 12. | | | | |

Picture color inspection result: (reference color searching: 4)

| Number: | Color tone difference: | C | M | Y | K | Inspection result: | Confirmation: |
|---|---|---|---|---|---|---|---|
| 1. | 3.2 | −1 | −1 | −2 | 0 | OK | ☑ |
| 2. | 4.0 | −2 | −2 | −3 | 0 | OK | ☑ |
| 3. | 3.0 | 1 | 1 | 1 | 0 | OK | ☑ |
| 4. | 2.9 | −1 | −1 | −0 | 0 | OK | ☑ |
| 5. | 2.1 | −1 | 0 | −0 | 0 | OK | ☑ |

IMAGE INSPECTING APPARATUS AND IMAGE INSPECTING PROGRAM

TECHNICAL FIELD

The present invention relates to an image inspecting apparatus and image inspecting program for inspecting the reference-image and the inspection-image.

BACKGROUND ART

Conventionally, there is known an image comparing apparatus in which one threshold value is applied to the detected difference at difference points in detection portions of the reference-image and the inspection-image on inspecting images of final contract proof, printed matter, and so on. The threshold value is varied by operation input to change an image display, thus enabling easy detection of difference points (for example, see Patent Document 1).

CITATION LIST

Patent Literatures

Patent Literature 1: JP 2013-80524

SUMMARY OF INVENTION

Technical Problem

In the conventional image inspecting apparatus described in Patent Literature 1, however, each time the detection accuracy is not preferable, it is necessary to vary the threshold value and to inspect an image. As a result, it is difficult to obtain a desired detection result in one image inspection.

In order to solve the above problem of the prior art, an object of the present invention is to provide an image inspecting apparatus and image inspecting program which are constructed safely at a low cost and enable obtaining desired detection results in a single image inspection.

Solution for the Problem

An image inspecting apparatus of the present invention is an apparatus for comparing first image data created as data representing a reference-image acting as an inspecting reference with second image data created as data representing an inspection-image acting as a target to automatically extract a difference point between the first image data and the second image data, characterized by comprising a storage means for storing the reference-image and the inspection-image, an image processing means for establishing correspondences between at least a part of the stored reference-image as the first image data with at least a part of the stored target image as the second image data at a pixel level to perform an image matching processing, a difference detecting means for comparing the image-matched first and second image data to detect a difference between the first and second image data, an image producing means for comparing the difference with a plurality of threshold values to produce difference point representing image data at each threshold value, and an image inspecting means for performing an image inspecting process using the produced difference point representing image data at each threshold value.

In an embodiment of the present invention, the image processing means performs an image dividing process for dividing the reference-image and the inspection-image stored in the storage means into a plurality of region images before or after the image matching processing, each of the region images being used hereafter as a process unit, which is the first and second image data.

In the other embodiment of the present invention, the image processing means extracts the corresponding partial images of the reference-image and the inspection-image stored in the storage means, correlates them, and performing the image matching processing of the correlated partial images as the first and second image data.

In the further other embodiment of the present invention, the image processing means adapts one of the first or second image data to the other of the first or second image data using an image correction function when the image matching processing of the first and second image data is performed.

In the further other embodiment of the present invention, the difference detecting means compares separately the image densities and image tones of the first and second image data to detect the differences.

In the further other embodiment of the present invention, the image inspecting means determines a critical threshold value based on the compared results between the threshold values and the differences and produces difference point representing image data.

In the further other embodiment of the present invention, the image inspecting means produces difference point representing image data based on the compared results between the difference point representing image data at different threshold values.

In the further other embodiment of the present invention, the image inspecting means switch-displays the plurality of the difference point representing image data such that the difference point representing portions are visible in different display manner for every difference point representing image data.

An image inspecting apparatus of the present invention is an apparatus for comparing first image data created as data representing a reference-image acting as an inspecting reference with second image data created as data representing an inspection-image acting as a target to automatically extract a difference point between the first image data and the second image data, characterized by comprising a storage means for storing the reference-image and the inspection-image, an image processing means for establishing correspondences between at least a part of the stored reference-image as the first image data with at least a part of the stored target image as the second image data at the pixel level to perform an image matching processing, a difference detecting means for comparing the image-matched first and second image data to detect a difference between the first and second image data, and an image inspecting means for producing different point representing image data using threshold values, which differ at each threshold value, to the detected difference to thereby perform an image inspecting process.

In an embodiment of the present invention, regarding color tunes of the first and second image data, the difference detecting means converts CIEXYZ image or RGB image into L*a*b* values and thereafter converts L*a*b* values into color differences ΔE or CMYK.

An image inspecting program of the present invention is a program for comparing first image data created as data representing a reference-image acting as an inspecting reference with second image data created as data representing an inspection-image acting as a target to automatically detect a difference point between the first image data and the second image data, characterized by allowing a computer execute a process comprising a storing step for storing the reference-image and the inspection-image in a storage means, an image processing step for establishing correspondences between at least a part of the stored reference-image as the first image data with at least a part of the stored target image as the second image data at the pixel level to perform an image matching processing, a difference detecting step for comparing the image-matched first and second image data to detect a difference between the first and second image data, an image producing step for comparing the difference with a plurality of threshold values to produce difference point representing image data at each threshold value, and an image inspecting step for performing an image inspecting process using the produced difference point representing image data at each threshold value.

In an embodiment of the present invention, the image processing step performs an image dividing process for dividing the reference-image and the inspection-image stored in the storage means into a plurality of region images before or after the image matching processing, each of the region images being used hereafter as a process unit, which is the first and second image data.

In the other embodiment of the present invention, the image processing step extracts the corresponding partial images of the reference-image and the inspection-image stored in the storage means, correlates them, and performing the image matching processing of the correlated the partial images as the first and second image data.

In the further other embodiment of the present invention, the image processing step adapts one of the first or second image data to the other of the first or second image data using an image correction function when the image matching processing of the first and second image data is performed.

In the further other embodiment of the present invention, the difference detecting step compares separately the image densities and image tones of the first and second image data to detect the differences.

In the further other embodiment of the present invention, the image inspecting step determines a critical threshold value based on the compared results between the threshold values and the differences and produces difference point representing image data.

In the further other embodiment of the present invention, the image inspecting step produces difference point representing image data based on the compared results between the difference point representing image data of different threshold values.

In the further other embodiment of the present invention, the image inspecting step switch-displays the plurality of the difference point representing image data such that the difference point representing portions are visible in different display manner for every difference point representing image data.

An image inspecting program of the present invention is a program for comparing first image data created as data representing a reference-image acting as an inspecting reference with second image data created as data representing an inspection-image acting as a target to automatically extract a difference point between the first image data and the second image data, characterized by allowing a computer execute a process comprising, a storage means for storing the reference-image and the inspection-image, an image processing means for establishing correspondences between at least a part of the stored reference-image as the first image data with at least a part of the stored target image as the second image data at the pixel level to perform an image matching processing, a difference detecting means for comparing the image-matched first and second image data to detect a difference between the first and second image data, and an image inspecting means for producing different point representing image data using threshold values which differ for every partial region value to the detected difference to thereby perform an image inspecting process.

In an embodiment of the present invention, regarding color tunes of the first and second image data, the difference detecting means converts CIEXYZ image or RGB image into L*a*b* values and thereafter converts L*a*b* values into color differences ΔE or CMYK.

In the other embodiment of the present invention, the threshold value includes a simple threshold value for evaluating in a condition of single threshold value and a multiple threshold value for evaluating in a condition of a plurality of threshold value.

Advantageous Effects of Invention

According to the present invention, it is possible to provide an image inspecting apparatus and image inspecting program which are constructed safely at a low cost and enable obtaining desired detection results in a single image inspection.

BRIEF DESCRIPTION OF DRAWINGS

FIG. 16 is a diagram illustrating the front page of the inspection evaluation report in the inspection result report.

DESCRIPTION OF EMBODIMENTS

There will be described an image inspecting apparatus and image inspecting program according to embodiments of the present invention in detail with reference to the accompanying drawings. The following embodiments do not limit the present invention recited in claims, and all combinations of characteristics explained in the embodiments are not necessary to the solving means of the present invention.

[First Embodiment]

Figure 1:
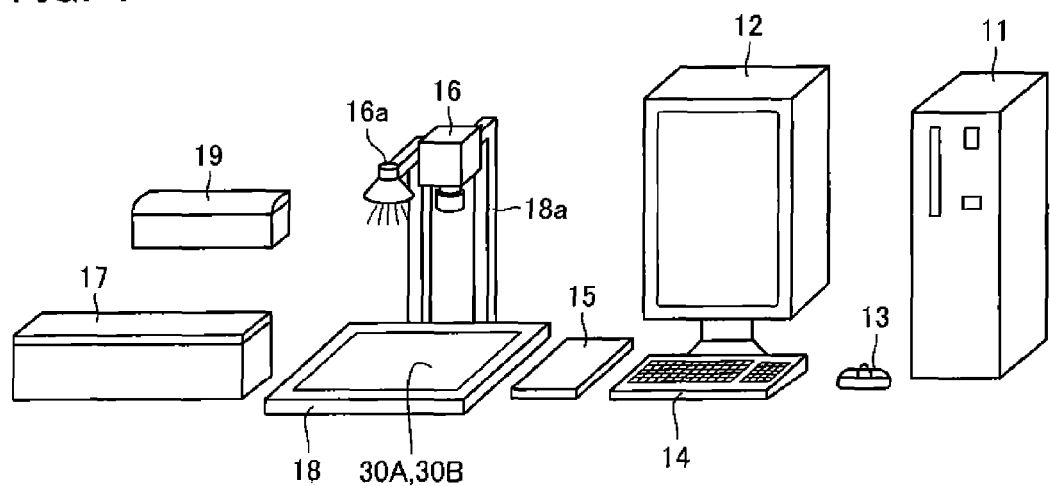
FIG. 1 is a block diagram illustrating an entire configuration of an image inspecting apparatus according to a first embodiment of the present invention.
Figure 2:
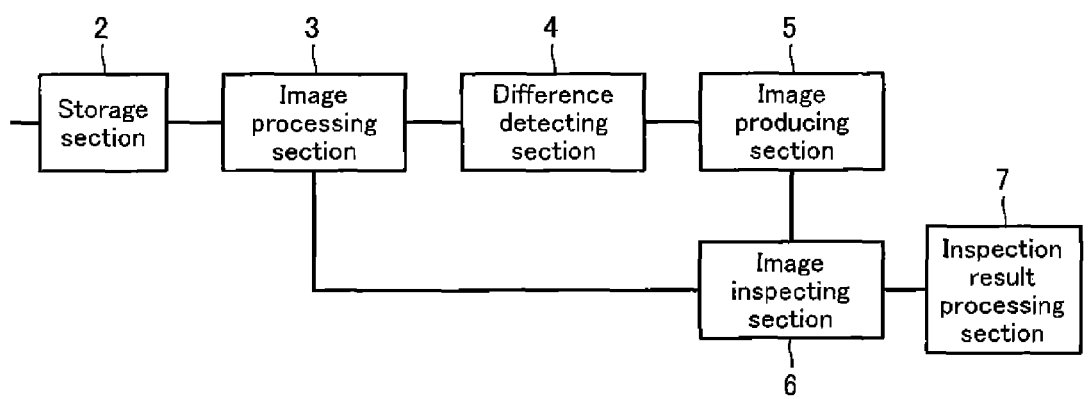
FIG. 2 is a block diagram illustrating the function of the image inspecting apparatus shown in FIG. 1.
Figure 3:
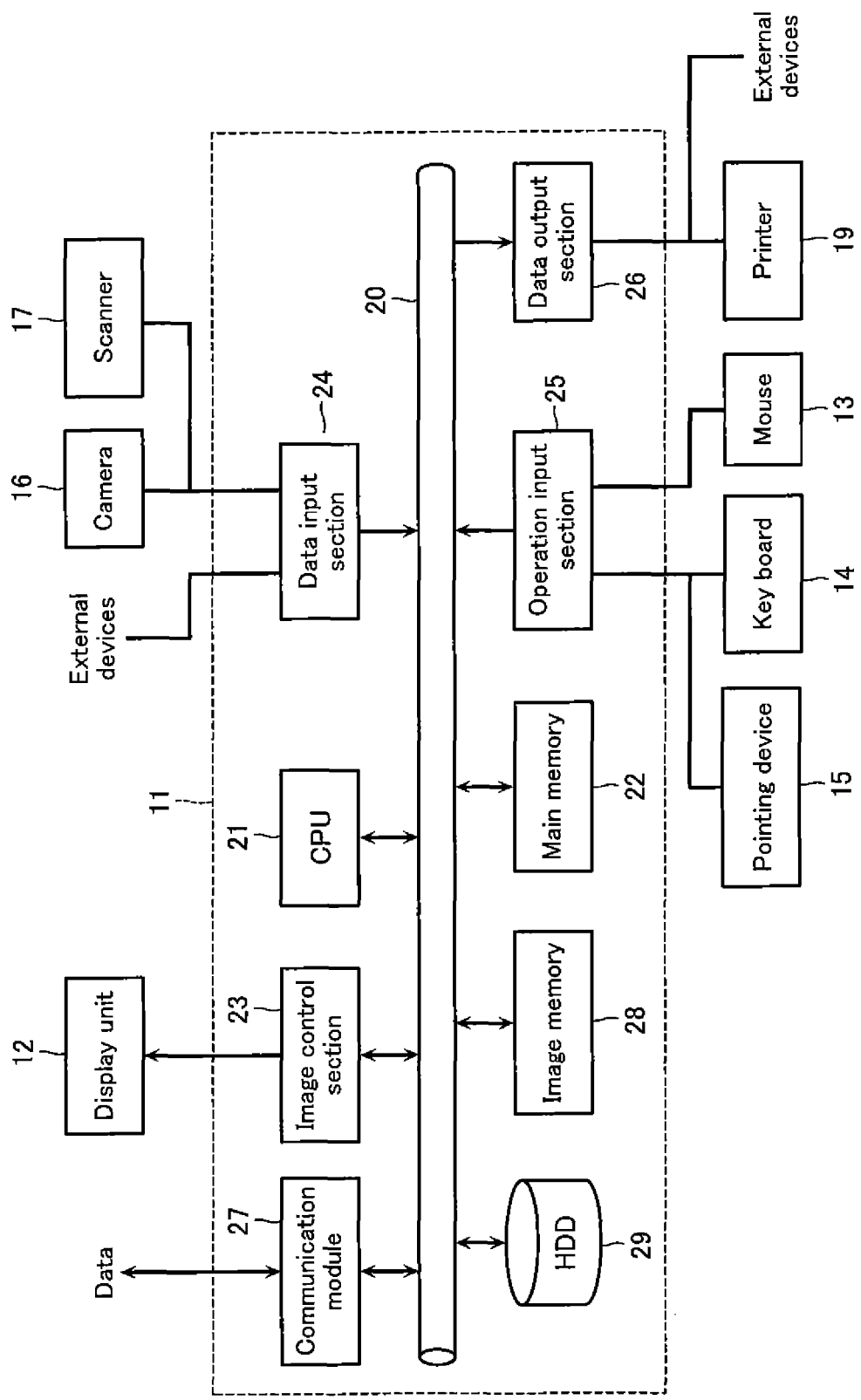
FIG. 3 is a block diagram illustrating the structure of the image inspecting apparatus shown in FIG. 1.

FIG. 1 is a block diagram illustrating an entire configuration of an image inspecting apparatus according to a first embodiment of the present invention. FIG. 2 is a block diagram illustrating the function of the image inspecting apparatus shown in FIG. 1. Further, FIG. 3 is a block diagram illustrating the structure of the image inspecting apparatus shown in FIG. 1.

As shown in FIG. 1, an image inspecting apparatus 10 according to the first embodiment is provided with a personal computer (PC) 11, a display unit 12 including a liquid crystal display (LCD), TFT, organic EL, and so on. The image inspecting apparatus 10 includes an input device such as a mouse 13, a keyboard 14, a pointing device 15, and so on.

Further, the image inspecting apparatus 10 is provided with an image input device such as a camera 16 as an image pick-up means and a scanner 17 as a scanning means, a printer 19 as an optional image output device, and a worktable 18 on which various kinds of objects to be imaged by the camera 16 under an illuminating light source 16a are mounted.

Both of the camera 16 and the scanner 17 may be connected to PC 11. Alternatively, either one of the camera 16 or the scanner 17 may be connected to PC. The camera 16 is attached to PC 11 by means of a support flame 18a such that it can pick-up various kinds of objects at an optional distance from, for example, the worktable 18 and the illuminating light source 16a and at an optional angle with them, and can be movably arranged. Preferably, the scanner 17 may be provided with a medium reading table (not shown) for reading at the same position and a table or mechanism for ejecting a paper.

The image inspecting apparatus 10 compares first image data created as data representing the reference-image acting as an inspecting reference with second image data created as data representing the inspection-image acting as a target to automatically extract a difference point (including dusts and stains) between the first image data and the second image data. The first image data includes printing image data of binary value or multiple value output from a raster image processor (RIP) apparatus. The first image data and second image data include a print image in the color conditioning state, a normal print image, and image data or image data for printing prepared by DTP software before printing.

The reference-image refers to the image printed on a reference medium among various kinds of media, which is a final proof print-proofed by a printing company and a client, or the image formed of image data for printing. The inspection-image refers to the image data before printing on an inspection medium such as a printed matter or formed of image data for printing, or the image printed on an inspection medium. The reference-image and the inspection-image include all visible images such as a character, numeral, figure, symbol, crest, photograph, code, color chart of IT8, and color control strip for color adjustment. There are cases where they include the image formed of data such as an invisible electronic watermark.

The reference medium and inspection medium include flat sheets made of various kinds of materials or papers with a slightly uneven surface, polyvinyl chloride, cellophane, PET, polypropylene coated matter, cloth, metal, evaporated paper, resin, wood, and stone in addition to the proof sheet and the printed matter. Further, colorants, colored light, phosphors and so on includes a pigment such as an oil-based ink and paint, a dye such as an aqueous ink and dying solution, and a light-emitting article including a color display such as a liquid crystal display, EL display and laser display.

The shape of the medium includes various kinds of shapes of bottles, cans, PET bottles, pots, dishes, household electrical appliances and so on, which can be processed by printing or coating, and a tablet, plate parts of instrument, electronic board and so on, which is directly printed or attached by welding. The medium includes products each having an image such as a color band, pattern, illustration, photograph, picture, letter, and so on. Examples of utility in general printing process are described hereinafter.

The image inspecting apparatus 10 is constructed as shown in FIG. 2. That is, as shown in FIG. 2, the image inspecting apparatus 10 includes a storage section 2, an image processing section 3, a difference detecting section 4, an image producing section 5, an image inspecting section 6, and an inspection result processing section 7. The storage section 2 stores temporally or permanently the reference-image and the inspection-image. The comparing inspection software of the image inspecting apparatus 10 has an inspection region setting function, threshold value setting function, an image matching function, an inspection result image reserving function, and inspection operation information sheet function.

The image processing section 3 performs an image matching processing of establishing correspondences between at least a part of the stored reference-image as the first image data with at least a part of the stored target image as the second image data at a pixel level. The difference detecting section 4 compares the image-matched first and second image data at an optional threshold value to detect a difference between the first and second image data. The image matching is synonymous with image overlaying. Further, the threshold value includes "a simple threshold value" for evaluating in a condition of single threshold value and "a condition threshold value" for evaluating in a condition of a combination of a plurality of threshold value (for example, different threshold values corresponding to upper limit, lower limit, and color). Hereinafter, 'threshold value" includes both the threshold values. "The simple threshold value" includes one "single threshold value" and at least two "multiple threshold values". "The condition threshold value" includes one "condition threshold value" and at least two "condition threshold values". The threshold value may not be set, or may be set to zero, regarding an uninspected region In the image processing section 3, when the image data obtained from the camera 16 is compare-inspected, for example, with the digital data for printing, an input image may be distorted due to aberration of a lens to cause position shift of the input image in the right and left portions and upper and lower portions in the image matching of the reference-image and inspecting image. In the case of the image data obtained from the scanner 17, position shift of the input image may cause similarly due to aberration of a lens and scanning irregularity in the image matching of the reference-image and inspecting image.

In this case, when the shift is small, the image to be comparative-inspected is divided into matrix, and the divided images can be matched, or it is expanded, shrunk, or rotated, and the images can be matched (in a complex manner). However, when the sizes of the images or positions of the image portions are largely and irregularly different, image matching may not be occasionally performed.

Under the circumstances, the directions are issued so that 4-15 points such as a center point and register marks for register control positioned in the right, left, upper and lower portions in the printed matter are overlapped, or cross portions of L letter shape or cruciform of angular register marks (trimming mark) in four corner portions are selected to perform an image control such as a deformation correction of trapezoid and so on, thus enabling image matching easily. Alternatively, the input image may be divided into a matrix or optional shape, and divided units are matched. It may be possible to automatically select characteristics of each image and to perform processing of image distortion correction. It is necessary to correct the read image since irregularity of read speed easily occurs. However, when the misalignment of the image exceeds a prescribed degree, a mechanism of preventing image matching may be employed.

The image producing section 5 produces different point displaying image data at each threshold value in order to further compare a plurality of different point displaying image data which produce differences in a plurality of threshold values (TH1-THn) with each other. The image inspecting section 6 perform an image inspection processing using the produced image data displaying different points at each threshold value. The image control associated with image matching in the image processing section 3 includes various kinds of image corrections such as thickening or thinning of lines or images and tone correction, and a color correction such as a color conversion using a profile.

Accordingly, the image data subjected to image correction processing can be precisely inspected in regard to letters and tone. The inspection result processing section 7 produces an inspection result report obtained by integrating a difference point displaying image of difference point representing image data produced in the image producing section 5, an image based on the inspection result difference point displaying image in which a marking frame is added to a difference image display or difference image corresponding to the optimum threshold value selected in the image processing in the image inspecting section 6, and number of difference points, and so on.

The difference point refers to the following matter. That is, the difference point refers to all the matter having a difference in an image such as a character, picture, and figure, and includes a print error such as a character missing, dust, dirt, and so on, an image error such as a shift or noise of a line, character and image shape in the output image generated due to difference in matching error or RIP processing, and corrected portion of a character and figure. These are called as difference point as a whole hereinafter.

The image matching is performed at a pixel level. For example, a dot of the image is a minimum unit forming the image and is simple physical point information. In addition, a pixel of the image is a minimum unit forming the image and is generally used as a synonym for the dot. However, in this embodiment, the pixel means a minimum unit or a minimum component having color information (a color tone or a grayscale level) when PC 11 treats the images. Therefore, one dot is one pixel in the case of a monochrome image. In the case of a color image, RGB forms one pixel, CMYK forms one pixel, XYZ forms one pixel, and L*a*b* forms one pixel. Since the image matching can be performed also at a level smaller than one pixel, in the case of a level smaller than one pixel, it is possible to display the matched image aligned at a precision of an error level smaller than one pixel by dithering with shading of the image.

Color information may include, for example, CIELAB (L*a*b*) values, CIEXYZ values, a Munsell display value, a spectral reflectance waveform, a spectral image, RGB value, CMYK value, a density value obtained by a filter, reflectance, transmittance, an infrared wavelength, an ultraviolet wavelength, an X-ray wavelength, and so on. In the L*a*b* color system, luminosity is represented by L*, and hue and chromes is represented by a* and b* as chromaticity. In addition, a* and b* indicate the directions of a color. For example, +a* indicates the direction of red, −a* indicates the direction of green, +b* indicates the direction of yellow, and −b* indicates the direction of blue. In the L*a*b* color system, as the value of each parameter increases, the definition of the color increases.

Though the color difference between the reference-image and the inspection-image can be determined by comparing the above-mentioned values, it can be also represented by ΔE of CIE1976 or CIEDE2000, and so on. When the image data of a printing machine or printing are represented by halftone dot percent, the halftone dot percent can be utilized as feedback information for color adjustment of a printing machine, or for color correction of printmaking in a design section, a prepress section and a printing factory.

The inspection result images are stored in an HDD 29. In the stored inspection result image, two images formed by image-matching the reference-image and the inspection-image and a difference image formed at each of a plurality of different threshold values are linked to each other as a layered structure of each of two images, and stored as data. Alternatively, one image formed by matching the reference-image and the inspection-image and a difference image formed at each of a plurality of different threshold values may be linked to each other as a layered structure of one image, and stored as data. Further, where an identification color is designated for the difference image formed at each threshold value, information of the identification color is stored in the header file of the inspection result image.

Even if PC has no comparative inspection software, the inspection result image can be viewed from PC in which simple display type viewer software is down-loaded and it is executed. The inspection result image is constructed such that a difference points obtained at a threshold value can be confirmed using the above-mentioned viewer software. For that reason, it is possible to display perspective corrected images of the reference-image and the inspection-image, to overlap-display the reference-image and the inspection-image, and to halftone-display the portions which are perfectly consistent in both the images. In addition, it is possible to select the difference image formed at the prescribed threshold value from a plurality of difference images and color-display the difference points, to alternately display a plurality of difference images formed at the different threshold values in different identification colors, and to alternately display a plurality of difference images formed in altered identification colors. Further, it is possible to set a threshold value of marking display. Where the threshold value is changed, it is possible to marking-display the difference image having a size (number of pixels) selected depending on the threshold value.

As shown in FIG. 3, a CPU 21 is built in the PC 11. The CPU 21 reads programs stored, for example, in a main memory 22 to allow variety kinds of operations to execute to the PC 11. Programs temporarily stored or permanently stored in the main memory 22 include variety kinds of software for image inspection. The software to be utilized includes a special purpose computer system, network web application, DTP application, database software, and sequence program, and so on.

CPU 21 is connected to an image control section 23, a data input section 14, an operation input section 25, a data output section 26, a communication module, and so on through a bus 20, and is constructed such that variety kinds of data and software are exchanged with external devices such as peripheral devices, remote installation devices, and so on.

An image memory 28 and a hard disk drive (HDD) 29 are connected to the CPU 21. The image memory 28 is used as a work memory in general image processing in addition to a memory for storing image data. An HDD 29 is constructed so as to temporarily and readably install and store variety kinds of data such as image data and so on, and variety kinds of programs.

The image control section 23 performs mainly a display control of the display image of the display unit 12. The data input section 24 inputs the image data imaged by, for example, the camera 16, the image data scanned by the scanner 17, and the image data obtained from external devices such as RIP and so on into the PC 11 to store them in the image memory 29 and HDD 29. The data input section 24 also controls the operations of the camera 11, the scanner 17 and so on.

The image control section 23 performs a light quantity control of the camera 16, a white balance control of RGB or CIEXYZ image input, a shading correction in the entire display screen of the display unit 12, a pixel number designation of the entire image, a level correction (range correction) of white and black, an RGB or CIEXYZ color range correction of the scanner 17, a designation of an input resolution, a scanning speed control, a color conversion using color profile, a correction of image gradation, and so on.

Regarding the input of the image data obtained from the external devises, the image control section 23 performs a resolution conversion, and a conversion of PDF data into TIFF-CMYK image or TIFF-RGB image. Thus, variety kinds of image data are converted into the same data format thereby to enable the image inspecting apparatus 10 to perform a comparative inspection.

The operation input section 25 assumes the roles of transmitting an input signal from the mouse 13, keyboard 14, pointing devise 15 and so on to the CPU 21 in which the operation demands to the image inspecting apparatus are controlled and restored (temporarily stored). The data output section 26 outputs data regarding variety kinds of image data or inspection result data formed by the CPU 21, data regarding inspecting operation information data, and so on to the printer 19 or the external device. The data output section 26 also controls an operation of the printer 19 and so on.

The communication module 27 is constructed so as to be capable of sending and receiving variety kinds of data, which can be handled by the PC 11, together with the above-mentioned variety kinds of image data and the data regarding the inspection result, through wire/wireless by means of a network line. The camera 16 includes variety kinds of line sensors such as CCD, a contact image sensor, and so on, and a special image sensor for infrared rays or ultraviolet rays in addition to a general CCD camera and CMOS camera. Further, it is possible to employ also an input device which can digitally convert the image from an analog camera.

Among a final proof or printed matter, there are ones printed by an offset printer and so on, in which ink is undried. Therefore, in some cases, the printed matter looks in different colors in the wet state and the dry state due to light reflection since the surface configuration of the oily ink adhered on the printing medium is viewed microscopically in different in a wet state and dry state. A PL (polarizing) filter can be attached to the camera 16 in order to prevent the influence. Where the PL filter is not used, an image processing or a color conversion table between the wet state and the dry state may be employed which exerts the same effect as the PL filter. The inspection of the printed matter on which ink is in the wet state will be described later.

The camera 16 may be used as an image pick-up means provided with, for example, an RGB filter, a CIEXYZ filter, an equivalent filter to CIEXYZ, and a spectrum filter. For example, where a color filter is used, an image color can be represented in a color system of CIERAB, Munsell, and so on. Alternatively, the camera 16 may be used also as an image pick-up means such as an infrared or ultraviolet camera, input device which can digitally convert a laser image, a magnetic image or an ultrasonic image, and so on.

The equivalent filter to CIEXYZ satisfies the condition in which the spectral curves are of convex shape with a single peak and without negative value in spectral properties (s1, s2, s3) satisfying CIEXYZ spectral properties, and have the same peak value and the foot portion with the minimum overlapping region.

The storage section 2 having a functional structure described above includes, for example, the main memory 22, the image memory 28 and the HDD 29. The image processing section 3 includes, for example, the CPU 21 and the image control section 23. Further, each of the difference detecting section 4, an image producing section 5, an image inspecting section 6, and an inspection result processing section 7 includes, for example, the CPU 21, the image control section 23, the main memory 22, and the image memory 28.

In the image inspecting apparatus 10 constructed above, the reference-image and the inspection-image used in the image inspection may be either of entire image or partial (region) image, and are supposed to be the image data which can be processed in the PC 11. That is, the image data (including image data for printing) hereinafter refer to image data from RIP and so on into which postscript data in DTP is input, image data formed in the CPU by means of variety kinds of application software, image data input from a camera or a scanner, image data received through network line, and so on. The image data form includes image data converted into PDF, TIFF, Bitmap, JPEG, PICT and so on, and image data of PPF data such as CIP3/PPF file, CIP4/PPF file and so on.

The image data include the image data converted from a digital camera or scanner, the image data such as DXF file, which is converted from a CAD device, a digital imaging and communication in medicine (DICOM) format, and so on. Further, the image data include a two-dimensional or three-dimensional image file which is converted after inputting or is corrected by the CPU.

Figure 4:
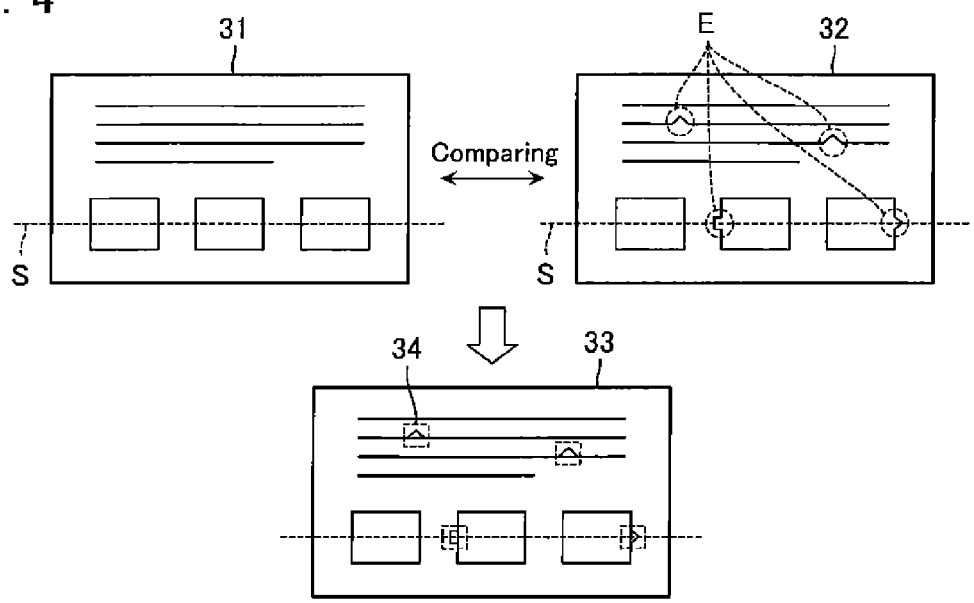
FIG. 4 is a diagram illustrating the concept of image detection in the image inspecting apparatus shown in FIG. 1.
Figure 5:
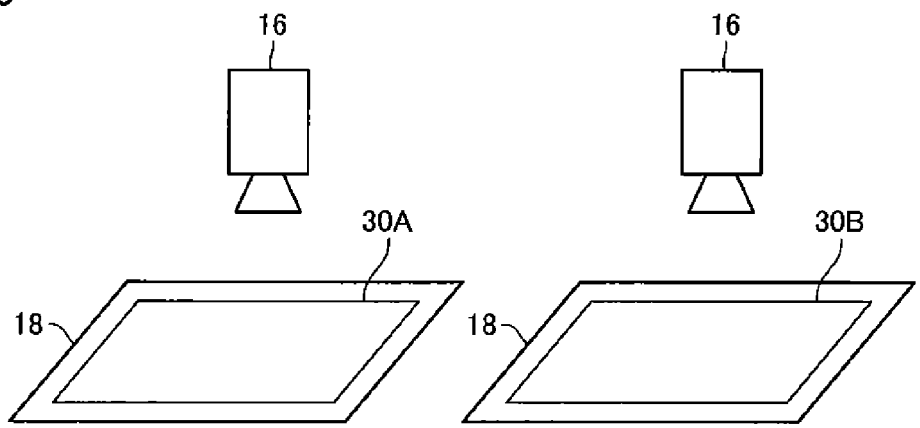
FIG. 5 is a diagram illustrating two camera input system applicable to the image inspecting apparatus shown in FIG. 1.

There will now be described an image inspection using the image inspecting apparatus 10 according to the first embodiment with reference to FIGS. 1-10. FIG. 4 is a drawing for explaining the concept of an image inspection in the image inspecting apparatus. FIG. 5 is a drawing for explaining a two-camera input system applicable to the image inspecting apparatus.

Figure 6:
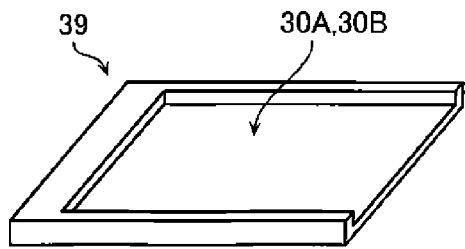
FIG. 6 is a diagram illustrating a medium supporting plate applicable to the image inspecting apparatus shown in FIG. 1.
Figure 7:
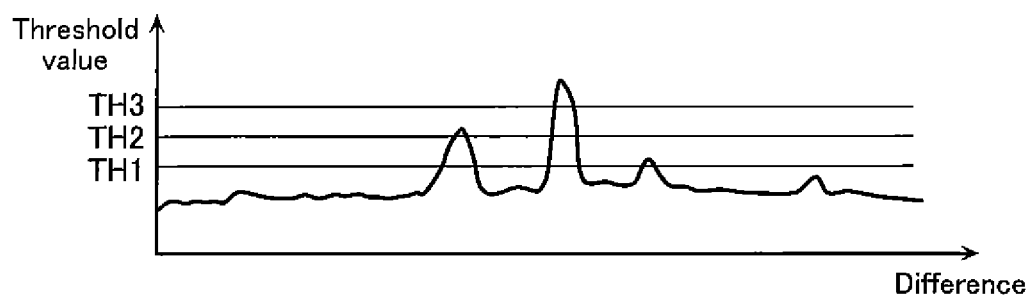
FIG. 7 is a diagram illustrating a correlation between a plurality of threshold values and difference information in the image inspecting apparatus shown in FIG. 1.
Figure 8:
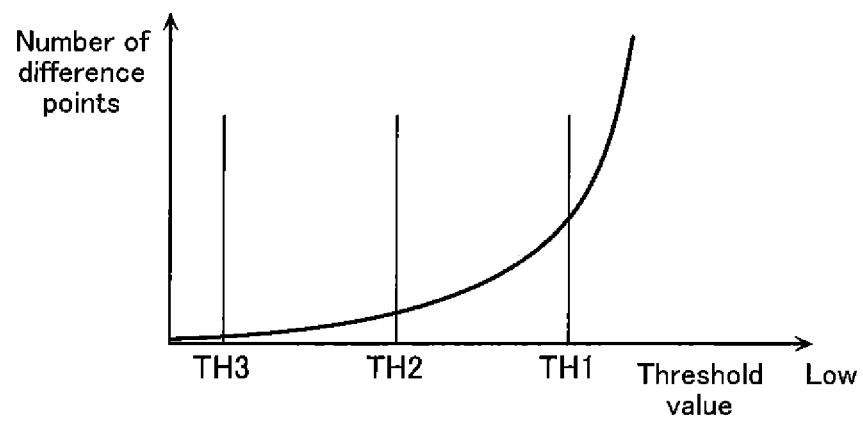
FIG. 8 is a diagram illustrating a change in number of difference points when the threshold value is changed in the image inspecting apparatus shown in FIG. 1.
Figure 9:
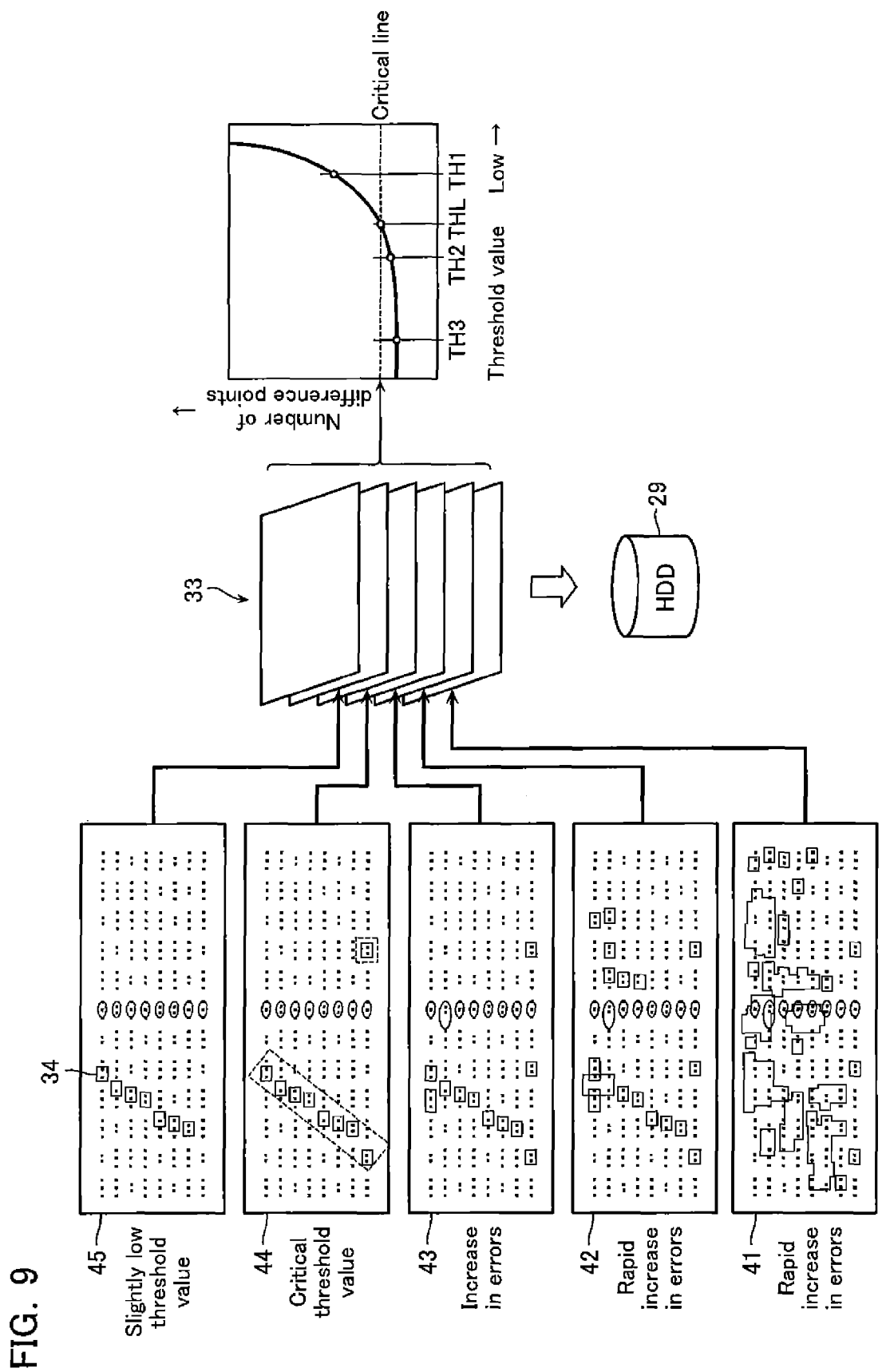
FIG. 9 is a diagram illustrating image data displaying a difference point at each threshold value, and limit threshold value.

FIG. 6 is a drawing showing a medium support plate applicable to the image inspecting apparatus. FIG. 7 is a drawing showing a correlation between a plurality of threshold values and difference information. FIG. 7 is a drawing showing a change in number of difference points depending on a change in a threshold value in the image inspecting apparatus. FIG. 8 is a drawing explaining a change in number of difference points depending on at each threshold value. FIG. 9 is a drawing explaining difference point display image data at each threshold value, which are produced in the image inspecting apparatus, and limit threshold values. Further, FIG. 9 is a drawing explaining the specific example of an image inspection using the image inspecting apparatus.

At first, a reference medium 30A such as a final proof or printed matter, on which the reference-image to be an inspection standard is printed, is loaded at the prescribed position on the worktable 18. And then, the reference-image is picked up by means of the camera 16 and the illuminating light source 16a, and the reference-image (first image data 31) obtained from the picked-up image is stored in the image memory 28.

Next, the reference medium 30A is removed from the worktable 18, and a reference medium 30B such as a final proof or printed matter, on which a inspection-image to be an inspection target is printed, is loaded at the prescribed position on the worktable 18 in the same manner as the case of the reference medium 30A. And then, the inspection-image is picked up by means of the camera 16 and the illuminating light source 16a, and the inspection-image (second image data 32) obtained from the picked-up image is stored in the image memory 28.

Incidentally, in the inspection example using a simple threshold value as shown in FIG. 4, the second image data 32 contains some difference points (error) E as described above in comparison with the first image data 31. The first and second image data 31, 32 may be obtained in one camera input system, and these image data 31, 32 may be correlated with a job code of an inspection job to form a pair file, which may be stored in a hot holder such as the HDD 29 and so on. In the same manner as above, it is possible to perform a continuous and automatic inspection at a simple threshold value or condition threshold value using the stored one pair files.

As described above, using the PC 11 and one camera 16 functioning as an image reading means or image obtaining means, at first, the reference-image and the inspection-image are picked up to produce the first image data 31 and the second image data 32, which are stored. The system for separately obtaining a picked up image using one camera 16 is called as one camera input system. In this system, it is better to read the reference-image and the inspection-image with the same size and resolution during image pick-up operation.

The first and second image data 31, 32 may be produced by two camera input system in which the image inspecting apparatus 10 equipped with two cameras 16 and two work tables 18 are employed, the reference-image of a reference medium 30A is picked up by one camera 16, the inspection-image of an inspection medium 30B is picked up by the other camera 16, at the same time, under the same illuminating light source 16a (not shown), and two picked up images are image-matched by the PC 11 to display them. Since, in this two camera input system, density and color of the input image displayed on the display screen (monitor screen) of the display unit 12 are mixed by additive color mixing, the image inspecting apparatus includes a device for converting additive color mixing into subtractive color mixing.

The images picked up by two cameras 16 are desirably regulated with the same reduced scale. Namely, the reference-image is picked up by one camera 16, the inspection-image is picked up by the other camera 16, and these picked up images are compared to determine enlarge-reduce degree of the images and regulated to the same size with the determined enlarge-reduce degree. The one camera 16 may be provided with a zoom lens which can regulate the size of the image and the distance between the lens and the object surface. Further, the apparatus may be provided with a moving mechanism for regulating individually moving distance of the lens in the XY direction.

In this two-camera system, even if inputs of size differences and positional shifts of the reference medium 30A and the inspection medium 30B occur, it is possible to perform a position correction and a size adjustment on a pixel level to image-match the images and inspect the image-matched images.

Incidentally, since it is possible to obtain the reference-image and the inspection-image in one picking up operation in the two-camera system, these images may be correlated with job code of inspection job as a pair file and stored in the HDD 29 and so on. Thus, it is possible to perform a continuous automatic inspection using the stored one pair file in the same manner as one camera system.

Alternatively, images may be obtained by one scanner input system in which the reference-image and the inspection-image are continuously or individually input by means of the one scanner 17 to obtain two scanning image, or by one camera one scanner input system in which the reference-image and the inspection-image are continuously or alternately input by means of the one camera 16 and the one scanner 17 to obtain a picked up image and a scanning image. In addition, PostScript data input into the data input section 24 may be subjected to RIP processing to obtain digital (image) data for printing, PFD data, and so on. And then, the first and second image data 31, 32 may be produced in order to inspect by hybrid system using the above-described input image from the different machine or image data to be compared. Also in these systems, it is possible to adjust to become same size lengthwise and breadthwise or to perform angle correction of two input images, thereby to perform individually inspection or continuously automatic inspection.

Where either the reference-image or the inspection-image is in a paginated state and the other is of a single page, the paginated page may be divided into single pages, or the image corresponding to the single page image may be extracted from the paginated page. And then, each of the single pages may be paginated, and the paginated pages may be image-matched.

Further, in the input medium used in scanner input or camera input, there is a case wherein an individual page image forming an eight-pages-paginated page is not visible to the naked eye in the correct position at a proper angle, and paginated in disorder. Furthermore, there is occasionally an error of a print size in each of the paginated pages. In these cases of image matching and difference inspection, the paginated images are divided in each page, matched in each page and subjected to difference inspection.

There will be described the case wherein a thin paper is printed on both the sides. In this case, co-called "bleedthrough" generates on the side of the printed inspection-image, which affects the inspection. In the image correction for removing bleedthrough, the image transmitting through the medium is removed from the mirror image of bleedthrough to form the inspection-image. In this case, since the portion of the front image overlapped with bleedthrough image is affected by the back image, the back image is taken into the front image as the mirror image and the image transmitting through the medium is removed from the whole of the front image. In addition, a white partial image mask is added to the inspection-image, and then, the inspection-image is inspected.

Further, in both sided printing, where the images of the reference medium and the inspection medium are input by camera input and scanner input so as to reduce bleedthrough phenomenon, the image is input with a black or dark gray paper laid on the rear side of the medium, thereby to obtain an effect of reducing bleedthrough phenomenon. In scanner input, when the apparatus has a structure in which the inspection medium conveyed by means of a conveying roller passes along a portion (slid surface or surface) of the light receiving section of CCD, CMOS or a contact image sensor of the scanner, it is provided with a printing medium pressing roll or pressing plate having a function for feeding the printing medium, on the opposite side to the surface of the light receiving section through the printing medium. When the printing medium pressing roll or pressing plate is blackened or dark-grayed, it can be substituted for the black or dark gray paper to be laid on the rear side of the medium, and the image of the medium can be input with reduced bleedthrough.

There is the other application in which, concerning the first and second image data 31, 32 of the reference-image and the inspection-image, the reference-image and the inspection-image are stored in the image memory 28 or HDD 29 of PC 11, and the first and/or second image is read or readout by means of CPU 21 and the image control section 23 through the image memory 28, HDD 29, or network line to obtain the first and second image data 31, 32. Alternatively, it is possible to read or readout the first and second image data 31, 32 produced in external devices themselves.

Further, it is possible to take in the two images (reference-image, inspection-image), which are to be inspected, from the camera 16, and to include a density (brightness), tone (chroma, hue), contrast, or gamma in these image data using comparative inspection software temporality stored in the main memory 22. And then, the system may be configured to construct the system so as to set previously inspection accuracy such as displacement on an inspection setting table screen, convert the produced first and second image data 31, 32 into multiple or binary data, and compare these converted data.

In the case in which the input data of the reference-image and the inspection-image are different from each other in kind and are those of images of the outputs from a printer, laser printer, ink jet printer, and so on, the thickness and sharpness of images or lines of the produced first and second image data 31, 32 are occasionally different due to fluctuation caused by various factors such as kinds of output devises, output setting and output accuracy of the devices, color, material, and reflectivity of the surface of the output material, inspection wavelength range, kinds of the image, and so on.

Where the image quality and line thickness of the first and second image data 31, 32 to be compared are different from each other in this manner, two images of the first and second image data 31, 32 are matched (in the other image layer or the other layer) to be displayed on the screen of the display unit 12, and a position over the entire region or one or a plurality of the prescribed partial region in the displayed image is indicated by the pointing device 15 and so on. As a result, there is performed image adjustments which includes an adjustment of image quality such as density (brightness), tone (chroma, hue), contrast, or gamma, thickening of lines or images, thickening of images by means of rotation of image angle, thinning such as line processing into skeleton letters consisting of a central portion of a linear image and so on, and distortion of the image. Further, it may be possible to perform a prescribed filtering processing and image adjustment processing, and then perform a prescribed image processing including image correction processing such as color management for adjusting tone and image adjustment processing and so on.

Where sharpness of an image obtained by picking up small letters of alphabet such as "a" and "e" and numerals such as "6" and "8" is worse owing to a lens of an image pickup device, accuracy of a comparative inspection is actually inferior. Where thicknesses of letters and so on are different between two images to be inspected, image processing of taking up the central lines of linear image portions of letters is performed to obtain skeleton letters, and thereafter texts are comparative-inspected.

The inspector confirms with naked eye whether letter groups having different thickness are same or not while observing the controlled (alternate) images of two images matched with each other, and enclose and delimit the image recognized to be the same letter groups with a box using a pointing device to make PC and a comparative inspecting software recognize as dot images having the same size. And then, the inspector performs an image correction processing to adapt the thickness of the line to that of the reference-image or inspection-image. As a result, it is possible to equally evaluate the two images.

Where the images with different sharpness such as different thicknesses of lines in letter portions, different resolutions, and different images from printing image data and camera input, are compared with each other, different point display to be the inspection-image error appears owing to a slight difference of images.

So, in order not to sense minute difference generating in the outlines of the images too much, a fuzzy processing is added to control the inspection threshold value only in the outlines of the line images formed by linking a plurality of pixels, for example, at least scores of pixels. Where, however, linking pixels are few or one image is solely sensed from the linking pixels with concentration of 50% or less, inspection steps are programmed to not to subject to fizzy processing and thus sense a dust image. As a result, it is possible to separate line images from printing errors (inspection impurity) such as dust images. The fizzy processing values of letters and colors are individually set.

Such an image processing is performed by a method for controlling the images using an image correcting function, for example, using PC 11 in advance, controlling the first and second image data 31, 32 with intermediate value of thickness difference, adapting either one of image data to the other image data, and adapting the image data to at least either one of image data using tone curve correction or color table (profile) and color conversion engine. For example, ICC color profile for the exclusive use of input devices, a common profile such as JAPAN COLOR and so on can be used as a profile. If do so, since the number of difference points (errors) E can be reduced, it is possible to inspect images with high accuracy.

Where one bit data showing printing halftone dots is utilized as the reference-image or inspection-image, for example, the image data have occasionally halftone information which have a high resolution of 2400 dpi and a high data capacity, and are prone to generate a moire pattern on resolution conversion. In this case, since the data are large, it is necessary to convert the image into an image having a tone of 8 bits, to scumble the halftone image once, and at the same time to perform re-sharpening and resolution conversion of the image before image matching, thereby preventing the moire generation due to a halftone image.

Further, the images are rotation-processed in order to correct precisely an angle of the input image on imaging before image matching processing, and resizing-processed in order to make two images of the same size, thereby obtaining a composite color image of CMYK four colors. The composite color is the final image for printing and is used as the reference-image for comparing with a proofread paper or base data for printing (PDF or TIFF-CMYK image). As a matter of course, it is possible to use as the reference-image, which is a base image for printing, in order to use for random inspection of a printed sample.

Where change in white level, black level, and color reproduction in the image input device occur, the same result is not obtained even if inspection is performed using the same inspection threshold value. Since, in most cases, the cause is due to fluctuation in a camera or scanner which is an image input device, it is necessary to perform adjustment or calibration of the input device using an exclusive chart to perform a constant image reproduction.

The exclusive chart is the inspection-image adjusting chart as an inspection standard for keeping the limit threshold value constant so that the same inspection result are obtained anywhere the inspection is performed. The chart includes difference in character, slight shear, or difference in thickness among a row of characters which are different in thickness, style of type, or size (point) in order to inspect characters. Using this chart, it is possible to automatically detect the size of the character with which the partial region is found, automatically detect the inspection threshold value by previously designating the size of character.

The inspection-image adjusting chart for simplifying setting of the proper threshold value is prepared in order to confirm inspection quality with the precision demanded by an inspector using inspecting instruments. The inspection-image adjusting chart is effective in obtaining simply the optimum threshold value regarding inspection precision demanded for performing a comparative inspection, for example, between a first image and a second image.

Further, the inspection-image adjusting chart is composed of two charts consisting of a reference chart and an inspection chart which are compared. Furthermore, the charts are printed or output on the same medium to be used in inspection. The inspection-image adjusting chart includes elements such as an inspection size of characters, color difference, dirt and character losses which are printing faults, pinholes of an image, dust in printing, and so on.

This inspection-image adjusting chart is image data which are fundamentally one sheet, or a reference chart which is output from these data. In this chart, there are arranged characters or letters of Japanese and foreign language such as English having various size of 4 to 20 points in white background and black background, punctuation marks and other special symbols such as punctuation marks, a question mark, parentheses, an accent marks, ruled lines in table and so on, a color chart such as IT8, flat tint, and gradation. There are also arranged images such as pictures and illustrations, human face, black and white ceramic wares, character design, logo samples in the inspection-image adjusting chart.

Further, differently from the reference chart of the inspection-image adjusting chart, in the inspection chart, there are arranged those portions of letters or images which are different from each other in a typeface or a color, portions from or to which one letter or a few letters are removed or added, portions in which letters or images are replaced. In these portions, yellow solid images, light-colored characteristic solid density image or halftone image are represented in white background, or as outline characters. The inspection-image adjusting chart is useful to setting of inspection accuracy to various matters to be inspected.

As described above, the inspection-image adjusting chart, in which character size, density, hue, chroma to be detected as differences between the reference chart and the inspection chart are listed on several levels, is prepared, and regarding accuracy of characters and images for correction, threshold value levels detectable for density difference and tone difference to be detected are set.

When comparative inspecting is performed at a threshold value of allowable level allowing objects to be estimated as fair quality on the basis of each inspection-image adjusting chart of the reference-image and inspection-image and the printed image data thereof, it is possible to confirm a point size and tone difference of color of the characters which can be inspected, in terms of $\Delta E$ or CMYK %. And then, the threshold values at which a character size can be inspected, based on this threshold value, and tone difference allowable threshold values are transmitted to a printing factory, a prepress section and a business office, which are concerned in the printing process.

Further, where the image imported by the image input apparatus is used, setting of pre-processing of image matching is performed individually in order to correct size and distortion of images in accordance with characteristics of input devices arranged individually in each section, and the optimum inspection threshold value is utilized. Hereby, there are obtained advantages enabling a printing company to unify the quality management standard in interoffice or in relation with subcontract. It is also possible to use the image imported by the image input apparatus arranged in each branch office by utilizing the optimum inspection threshold value.

Where the first and second image data 31, 32 having printing halftone dots is produced from the scanning image of the scanner 17 or image picked up by the camera 16, moire may be occasionally generated depending on the reading resolution of the scanner 17 and camera 16. In this case, it is necessary to scan at the resolution which is adjusted not to generate moire by adjusting scanning resolution to the printing dots, or to perform dot blurring and sharpness highlighting by subjecting the reference-image and the inspection-image input or during input to unsharpening processing using a moire removing software. Alternatively, it may be better to print using a FM screen which shows unremarkable moire, at changed printing dots, or to obtain the inspection-image after digitalization.

Where the first image data 31 and the second image data 32 are the image data produced by reading the reference-image and the inspection-image printed on the reference medium 30A and the inspection medium 30B using a printer, by means of the scanner 17, trouble may happen when ink is not dried and is wet just after printing, as described above.

Namely, when the wet ink on the reference medium 30A and the inspection medium 30B is in contact with the transfer roller and image reading section of the scanner 17 during reading by the scanner, printing matter is occasionally read in a soiled condition. In such a case, it is not possible to precisely inspect the image.

So, as shown in FIG. 6, there is used a medium holding plate 39 which can hold the reference medium 30A and the inspection medium 30B such that they can be read in no contact with the transfer roller and the image reading section of the scanner 17. This medium holding plate 39 is bonded to the reference medium 30A or the inspection medium 30B by means of an adsorbing agent or adhesive agent, which is attachable to the medium holding plate 39 or detachable from the medium holding plate 39, or double-faced adhesive tape which is removable from the medium holding plate 39, thereby enclosing the medium by a mask box. By using the medium holding plate 39, it is possible to transfer the inspection medium by the transfer roller without soiling the inspection medium.

Thus, the medium holding plate 39 is set in the reading section of the scanner 17 to align on the reading surface thereof. As a result, even if the image surface faces upside down, it is possible to read the image without dropping of the proofs and printed matter from the board of the medium holding plate 39, thereby obtaining the scanning image.

Incidentally, when pores are bored in the medium holding plate 39 over the entire surface thereof, and the board is sucked from the under surface thereof to stick the inspection medium to the surface thereof, the medium holding plate 39 functions as a sticking board. In addition, since a sticking paper having a sticking function is put on the board of the medium holding plate 39, costly sticking equipment is unnecessary and the medium holding plate 39 becomes a low-priced and simple member. Further, it is possible to employ a system in which air blows against the underside of the board to push the paper onto the upper plate of the board, thus bringing the paper closely in contact therewith. These are conveniently applicable to all apparatuses necessitating for inspection.

Next, image matching is performed such that two image data each consisting of at least one part of the first and second image data 31, 32 recorded in the image memory 23 are image-matched at pixel level as described above. The two image data each includes the whole or part of the reference-image, and the whole or part of the inspection-image. In the image inspecting apparatus according to the first embodiment, two difference point images comparing images of the matched first and second image data 31, 32 on the display screen of the display unit 12 are matched in different colors, or exchange-displayed alternately (shift-display), the marking frames are shown in the same or different colors, and existence or nonexistence of the marking frames are shown alternately on the display screen. Further, it is possible to exchange-display (shift-display) alternately the difference point image and the image obtained by enclosing the difference point by the marking box, whereby an inspector can confirm easily the difference point image.

Since, specifically, the first and second image data 31, 32 are precisely image-matched, the image matching processing is continuously performed in two steps as an inner processing of the image matching such that the images are image-matched and corresponds to each other at pixel level. In the first step, preprocessing is performed to arrange matching environment. Namely, the correction such as thickening adjustment and thinning adjustment, and resolution adjustment on the common coordinate axis are performed, together with relative image size difference adjustment in the vertical and horizontal directions, removal of relative image distortion, image position correction, image size correction, and image angle correction. In the second step, image matching of alignment is performed using a variety of known techniques such as characteristic image matching, one point image matching, multipoint image matching, matrix image matching, and optical division image matching.

In operation, where it is not possible to perform the position adjustment, rotation angle adjustment, and resize adjustment regarding different images in one operation since adjustment ranges are too wide and beyond allowable adjustment ranges, as described above, additional adjustment (run-in adjustment) is programmed so as to perform at least two adjustment operations. The image control section 23 has a function of rotating freely the image at a certain angle fundamentally using 90 degrees as a unit angle in order to adapt the directions of input images of the reference-image and the inspection-image and to display the image in the direction of normal image on the monitor screen. That is, where the properties of the apparatus are changed, paginated pages are divided, or the inspection-image is multi-paged at different angle than that of the reference-image, the directions of the images are made even. Thus, the directions of the reference-image and the inspection-image can be made even by performing the setting of angles before and after inspection, the adjustment of rotation on inspection, or using a mirror function to the printed matter which can be input only from the back surface.

Though the particulars are described later, it may be possible to perform image division processing for dividing an image into a plurality of region images before or after image matching processing of the reference-image and the inspection-image. The region group data of the first and second images representing the divided regional images are considered as processing units in the following processing, that is, the first and second image data. The divided parts are inspected at one threshold value or a plurality of threshold values, displayed, and stored.

In operation, where the corresponding parts of the reference-image and the inspection-image are different from each other in size or sticking-up angle due to pasting of one or both of the reference-image and the inspection-image, the image is divided into partial regions in each of the corresponding partial regions automatically or by means of a pointing device, and the image matching is performed in each of the partial regions.

Furthermore, where page number is given to both the partial region images to be inspected, subsequently "A" is given to the reference-image, "B" is given to the inspection-image, and these are stored in a hot holder, on the basis of the division information of dividing a paginated A1-size image into A4-size images and a template including paginated page information, it is possible to perform a continuous automatic processing of inspection. Inversely, image combination of divided files is performed in order of single-truck or double-truck, or in accordance with the paginated image of printing job, on the basis of the paginated information, followed by inspecting on the entire surface.

In the reference-image and inspection-image stored in the image memory 28 or HDD 29, the same partial images of text or picture, namely the partial image including the same content elements constituting text and picture in the same position or the position corresponding to the content image of the partial region described later may be extracted by image inspection processing, and the reference-image may be correlated with the inspection-image, and the correlated partial images may be image-matched as the first and second image data 31, 32.

Subsequently, the image inspecting apparatus 10 according the first embodiment compares the image-matched first and second image data 31, 32 using comparative inspection software, extracts density (luminosity), tone (chroma, hue, or L*a*b* value, ΔE value), and misalignment, and detect difference between the image data 31, 32.

The difference may include color difference based on RGB value, CMYK value, CIEXYZ value, L*a*b* value and density which are color values of the image, color difference (ΔE, CIEDE2000) based on Munsell color system value, spectral value, reflectance-transmittance, an image obtained from infrared rays, ultraviolet rays, X-rays, and so on. Further, the divided color density and color tone of the first and second image data 31, 32 are separated to compare them and detect the differences, respectively.

Specific examples of separating density and tone include, for example, converting the first and second image data 31, 32 into L*a*b* value, and thereafter dividing L*a*b* value into L value and a*b* value, or separating luminosity, chroma and hue. As described above, data comparing may be performed between multi-value data or two-value data.

The color inspections before and after conversion may be performed by L*a*b*a-converting an CIEXYZ image or RGB image into data displaying a half tone % of CMYK or ink amount using a profile of an input device and a monitor profile of an output device and displaying them. The CPU 21 constituting the difference detecting section 4 functioning as the above-mentioned difference detecting means, regarding the tones of the first and second image data 31, 32, may convert the CIEXYZ image or RGB image into L*a*b* value, and thereafter perform color difference ΔE conversion or CMYK conversion to detect a difference image.

The difference is detected, for example, in the case where difference points (errors E) are located on the inspection-image line represented by the line segments S in the first and second image data 31, 32, as shown in FIG. 4. In the difference point displaying image obtained from the difference point representing image data 33, shown in FIG. 4, since the difference points (errors E) are located on the inspection-image line represented by the line segments S, the marking box 34 is shown so as to visually enclose the difference point displaying portions (error displaying portions).

After detecting the differences, the difference of the first difference image and the difference of the second difference image, which are detected on the basis of a plurality of threshold values (TH1 to THn), are compared as, shown in FIG. 7. Incidentally, these threshold values can be arbitrarily set or altered by input operation of inspector using the mouse 13, keyboard 14, pointing device and so on. Alternatively, it is possible to detect the image on the basis of threshold values of a several levels adjacent to the basically set threshold value. Further, it is possible to use a simple threshold value or condition threshold value, as described above.

where it is necessary to inspect severely only in a part of the entire image with high accuracy, a high threshold value is previously set only in a partial region such as an agate or two dimensional bar code as a part to be precisely inspected, which is different threshold value from that of the whole region, and batch inspection is performed simultaneously at a plurality of threshold values. It is also possible to divide the inspection-image area, set prescribed threshold value to the divided prescribed part while maintaining a standard threshold value in the other part, and inspect the image at a plurality of threshold values.

In the case where a plurality of difference images obtained using a plurality of threshold values on the whole image are compared, when the difference images are displayed continuously at each threshold value, it can be observed that number of difference point displaying parts increases or decreases. Since the difference points can be detected between the first and second image data 31, 32 at each threshold value, in which number of difference point displaying parts increases or decreases, it is possible to show the difference points as difference point displaying parts enclosed by the marking box 34 as described above. Incidentally, as shown in FIG. 8, as the threshold value becomes lower (inspection accuracy becomes severer), number of difference points obtained by comparing differences at a plurality of threshold values becomes larger. On the other hand, as the threshold value becomes higher (inspection accuracy becomes looser), number of difference points obtained by comparing differences at a plurality of threshold values becomes smaller. As described above, in the region not to be inspected, a threshold value is not set or set to zero.

When the partial region of the whole image is selected (set), batch inspection is performed simultaneously at a plurality of threshold values, and the difference point displaying image obtained at two or at least three threshold values are observed together with shift displaying, it is possible to easily select the threshold value which is optimum as the partial region image at a plurality of threshold values. Similarly, when, at first, it is desired to inspect each partial region of the inspection media to be a standard at an optimum threshold value, the reference-image and the inspection-image are divided equally, the divided images are inspected simultaneously in block at several low and high threshold values including a firstly set inspection threshold value. And then, the difference point displaying images obtained from the batch inspection result at several low and high threshold values are displayed singly or in a list, selected and stored, in order to select the optimum difference point displaying image from the displayed difference point displaying images. The threshold value of the selected partial region may be stored and used as a default value in the next inspection.

The display images of difference point identification color is stored in layers added to the difference point image file at each of a plurality of inspection threshold value levels corresponding to each individual partial region of the inspection-image, as the difference point displaying images of the inspection result (refers to difference point displaying images). Further, the stored difference point displaying images of the inspection result can be easily subjected to switching display and color separation display of each inspection threshold value always.

For that reason, even if the image is input for individual inspection, or the image is continuously input using a printer provided with input device to perform an in-line automatic inspection, it becomes easy to select an optimum threshold value from the number of the difference point at each of a plurality of threshold values. In addition, even if PC has not comparative inspection software, where simplified viewer software separately developed is downloaded in PC, it is possible to confirm differences of the difference point displaying images of the above-mentioned inspection result depending on the threshold value.

In the image inspecting apparatus according to the first embodiment, the present inventors focus attention on using the plural threshold values and prepare difference point representing image data which enable viewing of difference point displaying portions from the difference point displaying images at each threshold value. As shown in FIG. 9, the difference point representing image data 41 to 45 at each threshold value are represented in the difference point displaying images by means of the marking frame 34 so as to enable viewing of difference point displaying portions.

Accordingly, number of the marking frame 34 at each threshold value in the difference point displaying images, and the difference point representing image data 41 to 45, which are different in display form such as an area of the difference point portion, are produced in the example shown in FIG. 9. The difference point representing image data 41 to 45 produced at each threshold value may be stored in the image memory 28 or HDD 29 as inspection result difference point display image data 33 of layer structure.

The inspection-image is divided into partial regions, and a threshold value is given to each of the partial regions. Density difference, color difference, and tone difference in each partial region are judged, and these inspection results in each of the partial regions are displayed in the form of acceptance/rejection or O/X.

Where a necessary portion in the inspection-image is divided, the divided portion is inspected at the threshold value designated in each divided partial region, and the threshold value of the divided partial image is modified, the data can be stored at the modified threshold value. The subsequent inspection also is performed at the modified threshold value, and the position information and the threshold value of this divided portion are stored, registered, and read out to utilize it any time.

In the image inspecting apparatus 10, where the number of difference points are continuously observed at each threshold value based on the comparison results between the indifference images depending on the plural threshold values and the number of the marking frames, the number of difference points rapidly increases in some cases whenever the threshold value changes. Therefore, the threshold value just before the number of difference points rapidly increases at each threshold value may be determined as a critical threshold value using a prescribed algorithm for calculation, and the difference point representing image data 44 may be formed at the critical threshold value.

Incidentally, "critical threshold value" refers to a (optimum) threshold value, at which the difference point can be detected, and to a critical threshold value, at which minute difference in a portion of non-difference point cannot be detected. Further, the difference point representing image data, which are different from each other in threshold value (for example, difference point representing image data 41 and difference point representing image data 43), may be compared, and difference point representing image data may be produced based on these comparison results.

Furthermore, the image inspecting apparatus 10 performs various image inspection processing using the difference point representing image data 41 to 45 produced by, for example, comparative inspection software. The image inspection processing includes displaying the difference point representing image data 41 to 45 on the display screen of the display unit 12 in different colors (red, blue, yellow) so that the difference point displaying portions are visible. It includes alternately displaying or switch-over displaying in order the difference point displaying images at each of at least two threshold values, marking-displaying the difference point displaying image at each of a plurality of threshold values, ON/OFF-displaying the marking box enclosing the difference point, and displaying the image subjected to both the movement and marking. In addition, it is more preferable to make the difference point images easily visible by displaying a plurality of difference point displaying images each identified with an identification color in an overlapped or listed manner or displaying a plurality of difference point displaying images, to which ON/OFF function is added, in an overlapped or listed manner.

Thus, the threshold value is increased or decreased in order to reduce unnecessary detection of the difference points to a minimum, and thereby to find the optimum threshold value enabling to detect character missing, foreign particles, and flaws. In order to easily confirm the resultant alteration, it is necessary to switch and alternately display the marking state in the difference point display portion at the initial inspection threshold value and the marking state in the difference point display portion at the other threshold value. Alternately, it is necessary to switch and alternately display the images in one touch operation by means of a pointing device.

In the image inspecting apparatus 10, image inspections are performed simultaneously and collectively using the difference point representing image data 41 to 45 at each threshold value, thereby obtaining proper inspection results. As a result, the inspector can detect the difference points between the reference-image and the inspection-image (between the first and second image data 31, 32) by observing the difference point display images of the difference point display image data 33 represented on the display screen of the display unit 12 shown in FIG. 4. Therefore, anyone can easily perform the image inspection at a constant level in one inspection operation without mistake.

It was described hereinbefore that characters, tones and so on of the reference-image and the inspection-image are compared, and the difference point images representing the differences of the images of the corresponding parts are enclosed by the marking boxes and displayed. However, there are some cases where attenuation dirt of a paper to be inspected and bubble of vinyl resin, which are improper as an inspection medium, are observed. In this case, it is necessary to use first and second threshold values for inspecting a printed part and a third threshold value for inspecting a part of a medium such as a sheet. Further, since inspection of change in dirt or color in each color such as red, blue, and yellow is necessary, for example in inspection of color, there are some cases where $n_{th}$ threshold value is necessary.

On the other hand, in order to perform a simulation inspection so that different points are not displayed even though images are slightly different, multiple threshold values are utilized. For example, a threshold value is set to limit the number of displays of marking frames. The reason is that there is a density difference between characters having different thickness (Gothic typeface and Ming-style typeface) or between the same characters of digital image and the image picked up by camera. Simulation inspection is performed so as to recognize these images as the same images, not difference point images. For example, high threshold value is set to a character of high density together with cutting-off of high density, not so as to evaluate density exceeding a certain value. Thus, it is possible to perform the inspection which does not evaluate density difference due to difference in characters.

In addition, where a contrast of the image in a cut-in evaluation region, which becomes low density range, is reversed to an original value, the contrast may be increased linearly. In this case, however, a density is converted by means of Log conversion or square conversion ($y=x^2$) not so as to change an intermediate tone so much, to widen a density difference in noise level and the inspection-image. As a result, it is possible to inspect images without affecting the detection of difference point images even though a lower threshold value is further increased to remove much noise than usual.

Thus, marking display is performed so as to enclose a difference point image formed from the difference of a character and tone between the reference-image and the inspection-image by a box. When the other threshold value for limiting this marking display is set, it is possible to prevent from displaying a marking box enclosing the difference point image which does not necessitate to be counted as difference points. Further, when the threshold value for performing the other evaluation the inspection threshold value for forming the difference point image is set, dust or dirt is found and marker display is possible even if there is not display of the difference point image.

Incidentally, for example, where the marking frame 34 is not displayed in the difference point display portion in which difference points are present in the difference point display image, or where the marking frame 34 is displayed in the difference point display portion representing an undesirable difference point or unnecessary difference point, it is possible to add the marking frame 34 representing the difference point display portion to the difference point display image of the inspection result difference point display image data 33 displayed in the display screen of the display unit 12 or removed the marking frame 34 therefrom, by operating, for example, the pointing device 15 and so on.

Where the marking frame 34 is added, the image inspection range of the portion necessitating display of difference points is designated and the marking frame 34 is added, whereby difference points of the necessary image portion region are automatically corrected, extracted, and produced from the whole image, so as to obtain the threshold values enabling to detect difference points in the region of the difference point display portion corresponding to the marking frame 34. Contrarily, where the marking frame 34 is removed, the image inspection range of the unnecessary portion of display of difference points is designated and the marking frame 34 is removed, whereby the threshold values are automatically corrected, and the marking frame 34 of the necessary image portion is removed from the whole image, so as to obtain the threshold values enabling not to detect difference points in the region of the difference point display portion corresponding to the removed marking frame 34. In this case, it may be better to enable to display the trace of addition or removal of the marking frame 34.

For example, where the image inspection is performed in the first and second image data of the images representing characters, and excess or deficiency of one character or a few characters causes in the correct operation of characters, inspection of characters cannot be practically performed since, even if characters in the following row are same, all following characters are represented to be different. For that reason, the image inspecting apparatus 10 automatically extracts a character row region, if necessary, or reproduces inspection range including the image of excess or deficiency number of characters bay means of a pointing device, and can perform inspection again.

Further, the image inspecting apparatus 10 can perform image inspection in which prescribed color is attacked great importance. In particular, since Y (yellow) series color and light color even in 100% solid density are hard to be inspected, image inspection is performed using the following density value or L*a*b*. In this case, specifically, regarding the image input by means of input device such as camera 16, the first image data from a picked up image and the second image data are image-matched, the density and L*a*b* in an inspection range are detected from PPF data, PDF, 1 bit tiff printing data and so on, and difference comparison is performed between the density data from the above-mentioned PPF data and the density data of the second image data to inspect the images. According to this image inspection, reliable inspection can be performed.

The above-described processing is realized by, for example, an image processing means, a difference detecting means, an image forming means, PC 11 as an image inspecting means, comparative inspection software installed or stored in CPU 21 or main memory 22, and so on. The inspection result difference point display image data 33 and the difference point display image data 1 to 45 in each partial region are included in data regarding the inspection result, and the difference point display image based on these display image data 33, 41 to 45 can be displayed in the display screen of the display unit 12 together with, for example, data including characters, numerals and so on showing the inspection result having a prescribed GUI structure.

In the image inspecting apparatus 10 according to the first embodiment, as described above, the first and second image data 31, 32 are image-matched to detect differences, and difference point display image data are produced in each of a plurality of threshold values set to the detected differences. Since the image inspection is performed using these difference point display image data, it is possible to perform the following particular image inspection.

Figure 10:
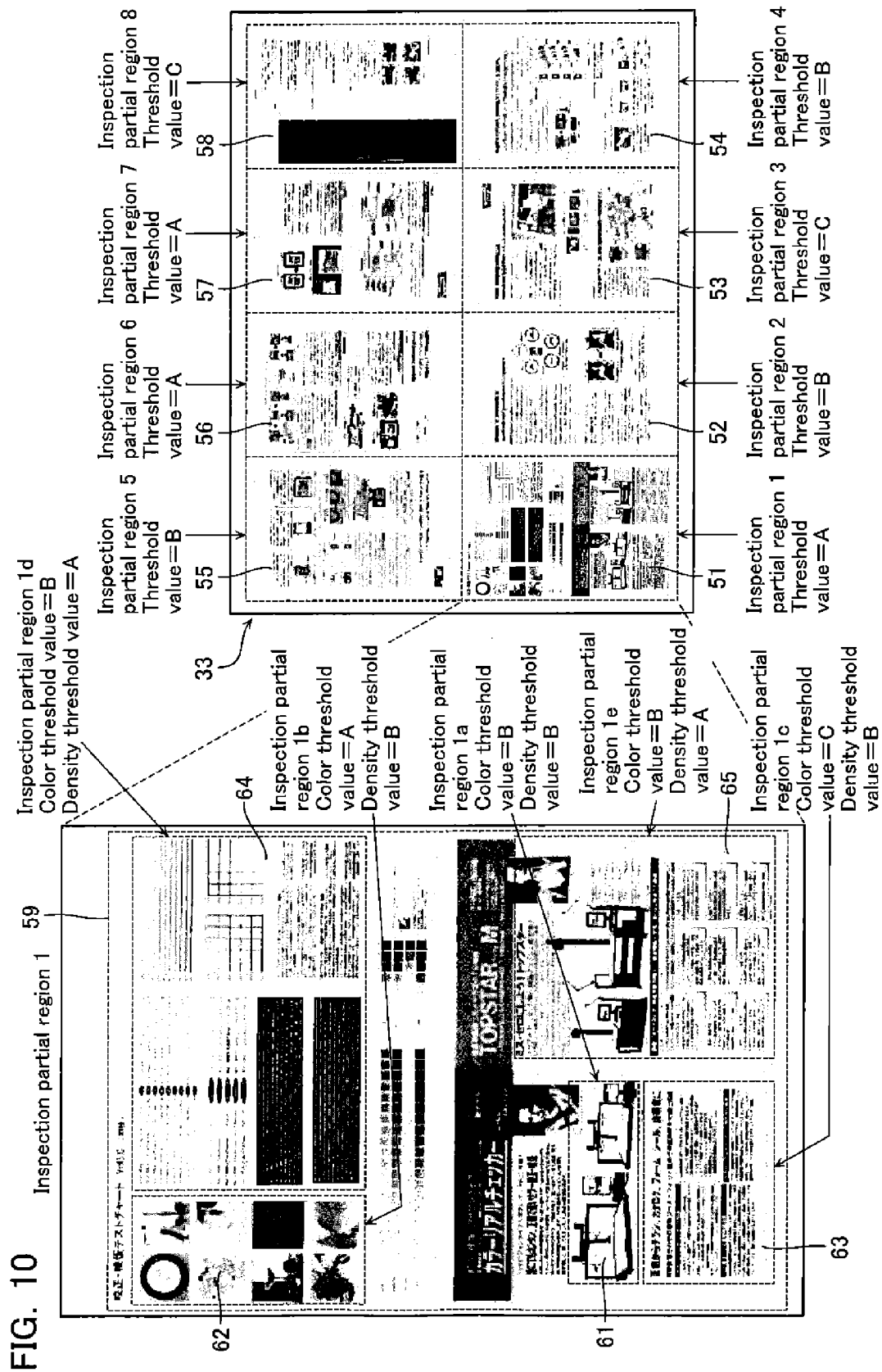
FIG. 10 is a diagram illustrating an example of a specific image inspection example obtained using the image inspecting apparatus shown in FIG. 1.

As shown in FIG. 10, for example, the difference point display images of the difference point display image data 33 displayed on the display screen of the display unit 12 are divided into eight matrix images of difference point display images 51 to 58 based on a plurality of region images corresponding to a plurality of inspection partial regions 1 to 8 and displayed. As described above, each of these partial regions constitutes a processing unit as the first and second image data 31, 32. Accordingly, the difference point display images 51 to 58 can be displayed, which represent the marking frame 34 (not shown) showing difference points due to the difference point display image data at different threshold values in each of inspection partial regions 1 to 8.

That is, in the example shown in Figures, the difference point display images 51, 56, 57 based on the difference point display image data of the threshold value A are displayed in the inspection partial regions 1, 6, 7 such that they are visible by means of the marking frame 34. In the same manner, the difference point display images 52, 54, 55 based on the difference point display image data of the threshold value B are displayed in the inspection partial regions 2, 4, 5, and the difference point display images 53, 58 based on the difference point display image data of the threshold value C are displayed in the inspection partial regions 3, 8.

The marking frames of the difference point display images 51 to 58 in the inspection partial regions 1 to 8 can be displayed in a state in which different identifying colors such as red, blue, yellow and so on are given, for example, at each threshold value A-C. The position and range of each of the inspection partial regions 1 to 8 can be arbitrarily set and changed by inspector's input operation using for example, mouse 13, keyboard 14, pointing device 15, and so on.

Thus, difference point display portions representing difference points (including image error, printing error, corrected portion, and so on) depending on different threshold values A-C every inspection partial regions 1 to 8 are displayed in the different point display image based on inspection result difference point display image data 33 which represents the inspection result of two image data 31, 32 of the reference-image and the inspection-image and is displayed on the display screen of the display unit 12. As a result, the inspector can easily detect the difference point between the first and second image data 31, 32 in each of the inspection partial regions 1 to 8 by seeing the display screen of the display unit 12.

Further, since the difference point display image data are produced using a plurality of partial region as a processing unit to perform an image inspection processing, it is possible for an inspector to freely change display form such as marking frame 34 and so on represented in the difference point display images 51 to 58 by input operating to fluctuate a threshold value every inspection partial regions 1 to 8.

Where, for example, an inspection accuracy of threshold value A in the inspection partial region 1 is changed low, display number and display area of the marking frame 34 on the difference point display image 51 decrease. Reversely, an inspection accuracy of threshold value A in the inspection partial region 1 is changed high, display number and display area of the marking frame 34 on the difference point display image 51 increase. It is possible to perform freely such an image inspection in each of the inspection partial regions 1 to 8.

As described above, since the divided partial region image can be used as a processing unit of the first and second image data 31, 32, it is also possible to set the inspection partial regions 1a to 1e or matrix-divided inspection partial regions 1a to 1e in the desired portion of each of the inspection partial regions 1 to 8, and to perform an image inspection using difference point display image data of different threshold values in each of the inspection partial regions 1a to 1e.

FIG. 10 shows a state in which the inspection partial regions 1a to 1e are set in the inspection partial region 1 in which, for example, the difference point display image 51 is represented, and the difference point display image 59 including difference point display images 61 to 65 is displayed. It is possible to represent the marking frames 34 and so on showing difference points based on the difference point display image data of different threshold values also in each of the inspection partial regions 1a to 1e.

In the example shown in Figures, it is possible to display the density threshold value B and the difference point display image 61 based on the difference point display image data of the color threshold value B in the inspection partial region 1a such that they are visible by means of the marking frame 34. In the same manner, it is possible to display the density threshold value B and the difference point display image 62 using the difference point display image data of the color threshold value B in the inspection partial region 1b, to display the density threshold value C and the difference point display image 63 based on the difference point display image data of the color threshold value B in the inspection partial region 1c, to display the density threshold value B the difference point display image 64 based on the difference point display image data of the color threshold value B and in the inspection partial region 1d, and to display the density threshold value B and the difference point display image 65 based on the difference point display image data of the color threshold value B and in the inspection partial region 1e. By doing so, it is possible to easily detect difference points between the reference-image and the inspection-image.

In the image inspecting apparatus 10, it is possible to deal with the reference-image and the inspection-image as first and second image data, even if they are images each representing a whole or a part, small and narrow region image which is obtained by dividing a partial image, or partial images corresponding to each other. Accordingly, image data representing various reference-images before inspection are stored in HDD 29, image data representing an image to be inspected are automatically searched and extracted from many images in HDD 29, based on the image data representing one image to be inspected, and the extracted data can be processed as first and second image data.

Specifically, for example, where image data representing an object to be inspected, such as characters, figures, pictures and so on, are input in PC 11, an image based on the input image data is produced as first image data. Then, image data representing an object to be inspected, such as characters, figures, pictures and so on, which is the same shape and corresponds to the image based on the input image data, are automatically searched, or image data linked to a predetermined job name are searched and extracted, and the image based on this image data is generated as second image data. These first and second image data are image-matched and inspected.

Regarding image searching, when a row of characters or a part of figure/image of a medium for inspecting printed matter is selected, a similar image is automatically extracted from rows of characters or picture images of the medium image to be compared, by means of job data command or direct image search processing, and difference thereof is inspected and displayed. Image search processing is performed such that intrinsic information of the image taken by PC or mobile information terminal (color information of image, intrinsic properties of an image such as a shape of an object in the image), or hashed image data may be searched and extracted. There may be employed techniques for searching images or information having similar or same objects stored therein.

The searching is performed in computerized images such as HP/electronic book, electronic leaflet, electronic newspaper and so on in the same manner.

Where in-line inspection is performed during printing, there is employed a system in which the inspection-image during printing is input to the reference-image which is a base image such as PDF, JPEG, and TIFF of a final proof, an inspected OK sheet, or a printed matter, and the reference-image and the inspection-image are image-matched, thus enabling to compare them. In the case of in-line inspection, a plurality of inspection results obtained at a plurality of threshold values set in a multiplex manner are displayed on a monitor screen in real time, and automatic inspection evaluation may be performed in the inspection setting condition, or an abnormal display on a monitor screen may be observed and estimated by an inspector (printing operator).

Where an inspection is performed in automatic batch processing, "A" is affixed to a job name, which is continuous in the numerical order of jobs having the corresponding same job name, assuming, for example, the reference-image as A image, and "B" is affixed to a job name, assuming the reference-image as B image. Threshold values of a plurality of inspection standards are set to one image or one image on each page, or partial image in partial region of each page, and continuous inspections are performed in automatic batch processing. In this case, a plurality of inspection threshold values may be set in a form of a threshold value of ±1 in a multiplex manner.

Then, paginated input images, which are paginated by a printer as a batch pretreatment, are divided into each of single pages based on pagination layout information, each of the divided images on one page are stored in a stacked state in the same file, and the reference-image and the inspection-image are stored in the same folder such that comparative inspection can be performed in one page unit by automatic continuous batch processing.

In this case, the same reference-image is used during one inspection. On the other hand, since the inspection-image may occasionally change when printing density changes, and dirt and missing character generate by fluctuation in printing situation, the reference-image is stored as an original image, the original image I used as the reference-image and the inspection-image are image-matched in real time, thus enabling to perform a comparative inspection of constantly precise image. Further, it is still better to obtain threshold values higher and lower than the value which seems to be an optimum threshold value, and to select a target threshold value from these values. Application examples are as follows:

It is necessary to automatically process a plurality of image data continuously in a corresponding job unit in order to improve efficiency of inspection operation. However, there are few cases in which none of the reference-image and the inspection-image is a single page, the one is a paginated image (considered folding of a printing medium), and the other is not also a single page and paginated in a two-page spread state.

The process includes a step (1) of dividing a paginated page into single pages. In the dividing step, a trimming step (2) is necessary to remove unnecessary image portion enclosing a page (the portion to be bled without being used as a printed portion). In order to automatically perform the trimming step, it is preferred to provide register marks to each page. Further, a setting step (3) of dividing process is performed. For example, it is necessary to input directions of any one of two-division right and left, division upper and lower, division upper and lower and four-division right and left, folding of head-to-head imposition or tail-to-tail-imposition, and designation of start page, and folding number.

Further, where a step (4) of automatically image-matching is performed, automatic searching is performed based on file name or thumb nail image using either of the reference-image or the inspection-image as a standard to obtain pair images. If one image is a digital image prepared by means of DTP software and the other image is an image input by means of a scanner or camera, a difference in density causes between both the images. When the images are different in density, they are color-measured by means of image surface color measuring function and converted into dot area ratios (%). And then, tone correction of the image data is performed so that the half tone density of one image data becomes same as that of the other image data. By doing so, it is necessary to avoid occurring of difference in images due to tone difference between both the images (5).

Next, the image to be inspected is divided into matrix pattern of a grid shape and image matching is performed. When an unsharpness level of characters or lines or a thickness of line is different, the density of the inspection-image seems different in the image portions of the characters or lines. Also in this case, the differences in density of the images and thickness of characters or lines due to unsharpness thereof are eliminated by correcting the density of an unclear image to equalize image density and uneven thickness due to blurring of characters or lines, thereby enabling to precisely inspect difference in characters or lines. Through these steps, comparative inspection is performed after image correction, whereby it is possible to perform an off-line image inspection and continuous image inspection more precisely.

There are two methods for dividing an area of printed picture image into matrix pattern and detecting difference in color tones of two images to be inspected by means of color measurement of image area in divided cell units. The first method includes dividing a whole image into square cells having 10 mm size and matrix pattern, further finely dividing each cell into parts in certain area ratio (for example 60%) set based on the center of each cell in order to remove an influence on colors of neighboring cells and to perform a precise color measuring, and performing a precise color measuring. For example, color difference values in the partial region of each cell are determined in a reading aperture size unit of 1 to 3 mm (freely settable) which can be recognized as a color. In this case, it may be possible to convert RGB value calculated every aperture in cell partial region into L*a*b* value, dividing the total color difference value obtained by adding L*a*b* values of aperture units by number of apertures to average L*a*b* values and determining CMYK % to perform color evaluation.

The second method includes selecting a square spot region of 1 to 3 mm size from an optional portion in the area of the picture image by means of a pointing device while watching a monitor screen, and performing color measurement. In this case, for example, color measurement is performed on a picture image portion to be half tone and full tone (dot 100%), gray portion, a screen tint portion, a gradation portion, and picture portion which have flesh color, single color (C, M, Y, K) or color approximate to secondary color (R, G, B), to determine difference values between the reference-image and the inspection-image. The tone differences in the entire image region are automatically analyzed to calculate corrected values to each tone.

Since the corrected values of tone due to difference in tones of the entire region of the image are calculated from the results obtained using either one of comparative-analyzing the tonality of the color by the above-described two methods, it is possible to automatically correct color regeneration of the same jobs and to eliminate inspection error of characters. If large differences in tone regeneration are generated between character region and picture image regions such as photographs, illustrations, figures and so on, or the direction of difference in density and tone of the tone correction is reverse, it may be possible to divide a region to be corrected one by one to correct different densities and tones. On the other hand, since it is necessary to detect tone differences in color inspection, the accuracy of color inspection can be maintained by comparing the images before correction of density tone and tonality of color.

Where an automatic inspection is performed in order to determine whether or not one part of an image portion (single image) as the reference-image is same as the inspection-image in which one part of the same image is laid out in multi-composition, the single images as the reference-images are temporarily called from a memory, image-matched with the image laid out in multi-composition, and subjected to comparative inspection, continuously one by one. In the same manner also on the occasion where the inspection-image is step-and-repeat composed image, the single images as the reference-images are extracted by cutting-out of inroad images, temporarily called from a memory, image-matched with the image laid out in multi-composition as the inspection-image, and subjected to comparative inspection, on each same position.

In this case, where the reference-image and the inspection-image are different in direction and size from each other, these images are rotated, subjected to resize processing, and image-matched with each other continuously one by one, whereby image matching of all images are performed. Where the direction and expansion rate of the inspection-image are apparent, parameter indication of characteristics, moving distance, the directions (rotating direction and rotating angle), expansion percentage and contraction percentage of the images to be image-matched is previously given to the reference-image or the inspection-image, and image matching and comparative inspection of the matched images are performed in order of the paginated images. Where images have at least two characteristic points, the characteristic points may be designated and image matching may be performed. Needless to say, automatic extraction of characteristic points may be performed, and the entire processing including image matching may be automatically performed. Further, the single images described above may be attached along the arrangement of the step-and-repeat composed image to convert the single images into another step-and-repeat composed image, and the other step-and-repeat composed image may be image-matched with the step-and-repeat composed image as the inspection-image to perform inspection.

There is a technique of so-called gang job in which a plurality of different printing jobs are ganged-up or step-and-repeat paginated in one printing impression and images are written in the machine plate of printing by laser irradiation, and printing is performed using it. This technique operates a plurality of printing steps as a job lot, lessens an unavailable blank space of a paper, and thus reduces a cost and time.

In the inspection operation of printed matter which is step-and-repeat paginated in a gang job, one edition to be printed is constructed by a plurality of customers in most cases. And so, it is desirable to input the image to be inspected in a unit of ganging edition and store it in one file. Further, since unequal single pages are occasionally arranged in one printing impression, after printing image data are individually input, the arrangement order of the reference-image and the inspection-image are identically brought into correspondence with each other, images to be inspected are moved automatically or by means of a pointing device, and image matching and comparative inspection are continuously performed at the same time. Where, in the ganging image inspection, the reference-image having the same arrangement as ganging arrangement is considered as the inspection-image, it can be applied to the in-line inspection during printing.

As described above, in the step-and-repeat pagination of a plurality jobs by ganging, it is necessary to inspect the reference-image of a plurality jobs and the inspection-image, which is single-image paginated or step-and-repeat paginated in each job of a plurality jobs. For example, it is assumed that 15 kinds of jobs of card printed matter are 15 reference-images. On the other hand, the same jobs are step-and-repeat paginated in each of 15 jobs, and 15 kinds of images are ganged on 40 faces. In this case, the image, in which the inspection-image corresponding to one of a plurality of reference-image is single-image paginated or step-and-repeat paginated, is automatically searched, and then image matching and inspection are performed. And successively, the image, in which the inspection-image corresponding to next one of a plurality of reference-image is single-image paginated or step-and-repeat paginated, is automatically searched, and then image matching and inspection are performed. After that, these steps are repeated till the last inspection of the reference-image and the inspection-image are performed. Even though job commands are previously indicated in an inspection operation information sheet described later, and jobs different for customers are step-and-repeat paginated and printed, it is possible to easily change the designation of the inspection threshold value. It is also possible to output individual inspection results for each customer, and transmit the inspection result to an appropriate person in charge.

Further, it is possible to step-and-repeat paginate the above-described reference-image in the same arrangement as that of the inspection-image, image-matched and inspected. In order to automatically search the above-described reference-image corresponding to ganging inspection and the single-image paginated or step-and-repeat paginated inspection-image to arrange images, it is possible to obtain position information in each single page image or step-and-repeat composed image with respect to each individual job image as the reference-image. As a result, an inspection position is automatically designated, and it is possible to perform image matching and inspection as a step-and-repeat composed image.

As described above, even though images include characters or figures of a foreign language, or an inspector cannot understand it, the image inspecting apparatus according to the first embodiment compares the reference-image and the inspection-image to detect a difference, and can simply and precisely inspect the images with high convenience. It is better to extract text data from the image by means of an optical character recognition (OCR) to inspect mutual text data.

[Second Embodiment]

Figure 11:
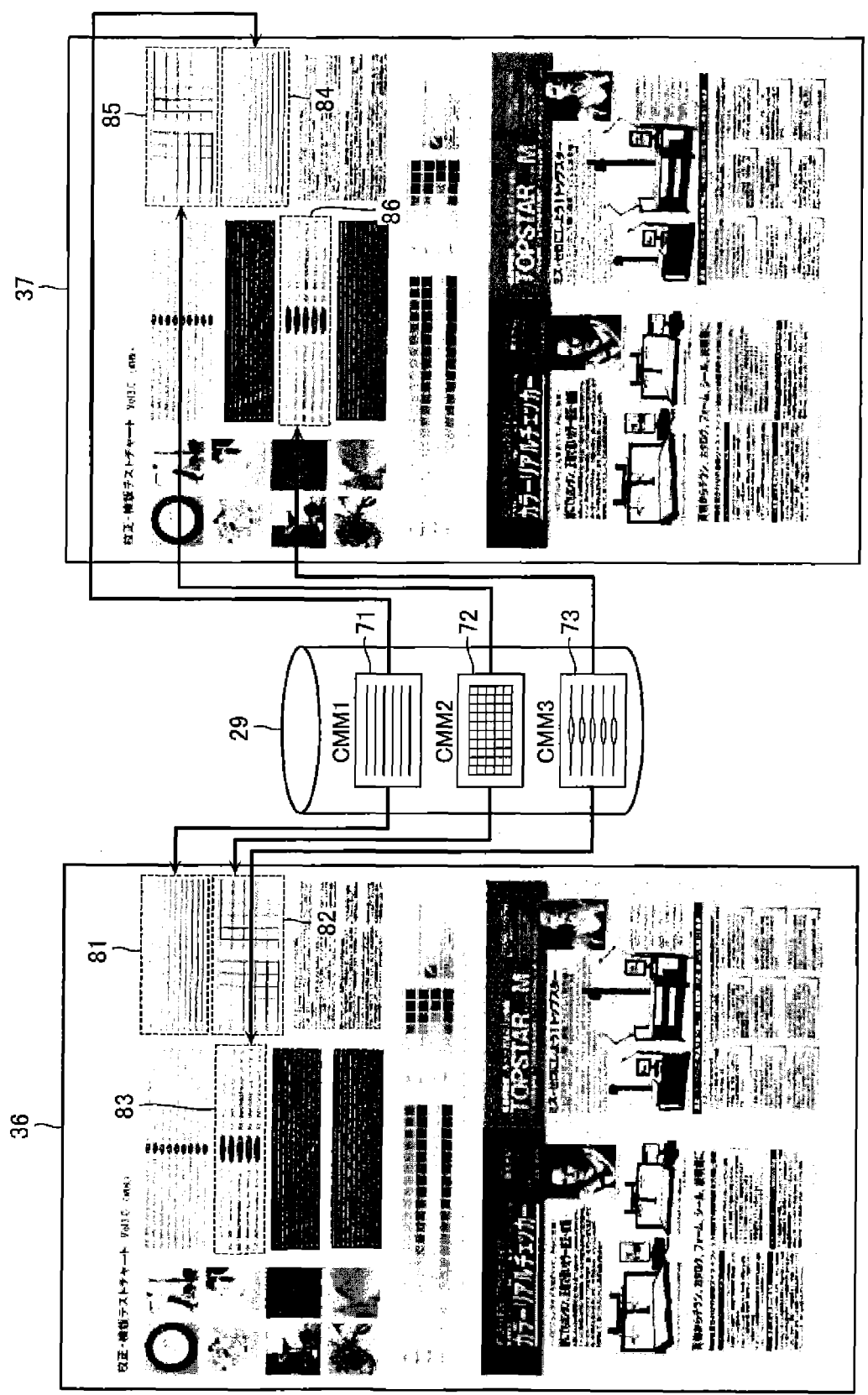
FIG. 11 is a block diagram illustrating an image inspection in an image inspecting apparatus according to a second embodiment of the present invention.

FIG. 11 is a view explaining an image inspection in the image inspecting apparatus according to the second embodiment of the present invention. The image inspecting apparatus according to the second embodiment can be implemented with the same structure and function as those of the image inspecting apparatus 10 according to the first embodiment. The second embodiment can perform an image inspection as follows:

The second embodiment relates to the case where partial regions are constructed in different layout from each other even if the reference-image and the inspection-image of the first and second image data, which are input and displayed on the monitor screen, have the same content. Further, comparative-mage inspections are performed using the same technique between a paginated multi-page image and an individual page image corresponding to the paginated multi-page image, or between a paginated multi-page image and the above-described ganging image. Image inspection regarding the partial region image is explained as follows:

The partial region images 71 to 73 of the inspection-image, which correspond to partial region images of the reference-image though they differ in layout, are correlated and image-matched with the partial region images of the reference-image. For example, commands CMM1, CMM2, and CMM3 for image inspection are linked and correlated as M1 partial region image, M2 partial region image, and M2 partial region image, respectively. And then, the correlated partial region images are subjected to image matching processing and the subsequent processing as the first and second image data.

In the inspection of the reference-image and the inspection-image which have the same contents and differ in layout as described above, when content elements of various partial region images 71, 72, 73 such as corresponding characters, pictures and figures in the first and second image data are compared to each other, corresponding parts to be compared in the reference-image are enclosed by boxes using a pointing device, corresponding region parts of the inspection-image are automatically searched. Alternatively, boxes for enclosing parts of the inspection-image are extracted and reproduced to designate by enclosing the corresponding region parts of the inspection-image by boxes and to link thereto. Then, those various partial region images are enclosed by boxes using a pointing device and linked using job names and branch numbers of the partial regions to correlate with each other, and the images, which correspond to the partial region layout, are enclosed by boxes are inspected. The position information of the partial region may be added together with the inspection-image. In the inspection results, either one of the reference-image and the inspection-image can be freely displayed.

When the range of the inspection parts of the reference-image are designated by a pointing device, the boxes representing the range and designated in the reference-image are copied and pasted into the same inspection region of the inspection-image, whereby two region images can be considered as the partial regions enclosed by boxes having the same size, and automatic image matching and comparative inspection of difference can be performed.

When the range of the inspection parts of the reference-image are designated by a pointing device, and image size of the same inspection region as that of the inspection-image and image position in the designated region are different from those of the reference-image, it is possible to correct the image size and image position, automatically match the images, and perform comparative inspection of differences.

Thus, as shown in FIG. 11, commands CMM1 to CMMn for image inspection correlate the partial region images constituted by the same design elements and having different layout from each other to enable comparative-inspection of the images.

After image matching, information is added to entire layout images constituting each of the partial region images 71 to 73, which are extracted and correlated to the commands CMM1 to CMMn for each image inspection, and stored in HDD 29. By doing so, it is possible to automatically extract the partial region images 71 to 73 of the reference-image and the inspection-image in the layout structures, which are different in design, on the reference-image medium 30A and the inspection-image medium 30B to perform image inspection described above.

When image inspection is performed in the layout structures which are different in design according to an inspection operation information sheet later described, job names and branch numbers of partial regions are written between for example, # and # after job name in the job commands for linking, and correlating are registered. And then, automatic inspection is performed from commands of the inspection operation information sheet. Further, it is better to store a plurality of layouts in a job unit as a layout template and reuse them.

Various partial region images 71, 72, 73 such as characters and pictures constituting the first and second image data are correlated to the layout boxes of the first and second layout templates 36, 37 and stored therein. CPU 21 can also extract image to be searched, correlated, and image-matched by image matching processing using pattern matching method, followed by subsequent processing. CPU 21 extracts the partial region image 71 of a layout region 81 from HDD 29 based on command CMM1, extracts a layout region 84 of a second layout template 37 representing the partial region image 71, and correlates it with the partial region image 71. And then, the correlated partial region images 71 are image-matched with each other as the first and second image data, followed by subsequent processing.

In the same manner, also based on command CMM2 for image inspection, CPU 21 extracts the partial region image 72 of a layout region 82 from HDD 29, extracts a layout region 85 of a second layout template 37 representing the partial region image 72, and correlates it with the partial region image 72.

CPU 21 extracts the partial region image 73 of a layout region 83 of the first layout template 36, and correlates it with the layout region 86 of the second layout template 37. After image matching, the commands CMM1 to CMMn for each image inspection are linked (correlated) to each of the partial region images 71 to 73, which is extracted and correlated thereto, and stored in HDD 29.

By doing so, it is possible to automatically extract proper threshold values to the partial region images 71 to 73 of the reference-image and the inspection-image in the layout structures, which are different in design, on the reference-image medium 30A and the inspection-image medium 30B. After that, image inspection may be also performed using the same threshold value.

Further, in a computerized content image such as a homepage prepared in connection with printed matter, an electronic book, an electronic leaflet, electronic newspaper and so on, corresponding characters, figures and images between the original layout and changed layout are automatically recognized using setting commands or linked, in type setting composition data which are obtained by inserting a text and image from data base (DB) into original layout and changed layout and laying out, and the differences are inspected and displayed.

As an example, there is mentioned a technique in which a search tag such as TEXT01, PICT01 and so on are attached to a text, figure, image and so on for the type setting composition, stored, and called from the type setting composition template such as DTP, HTML, XML, VML and so on to perform layout. Since the search tag effectively moves even if a design is changed, it is possible to realize an inspection before and after modification of design and an inspection between designs which are quite different.

[Third Embodiment]

Figure 12:
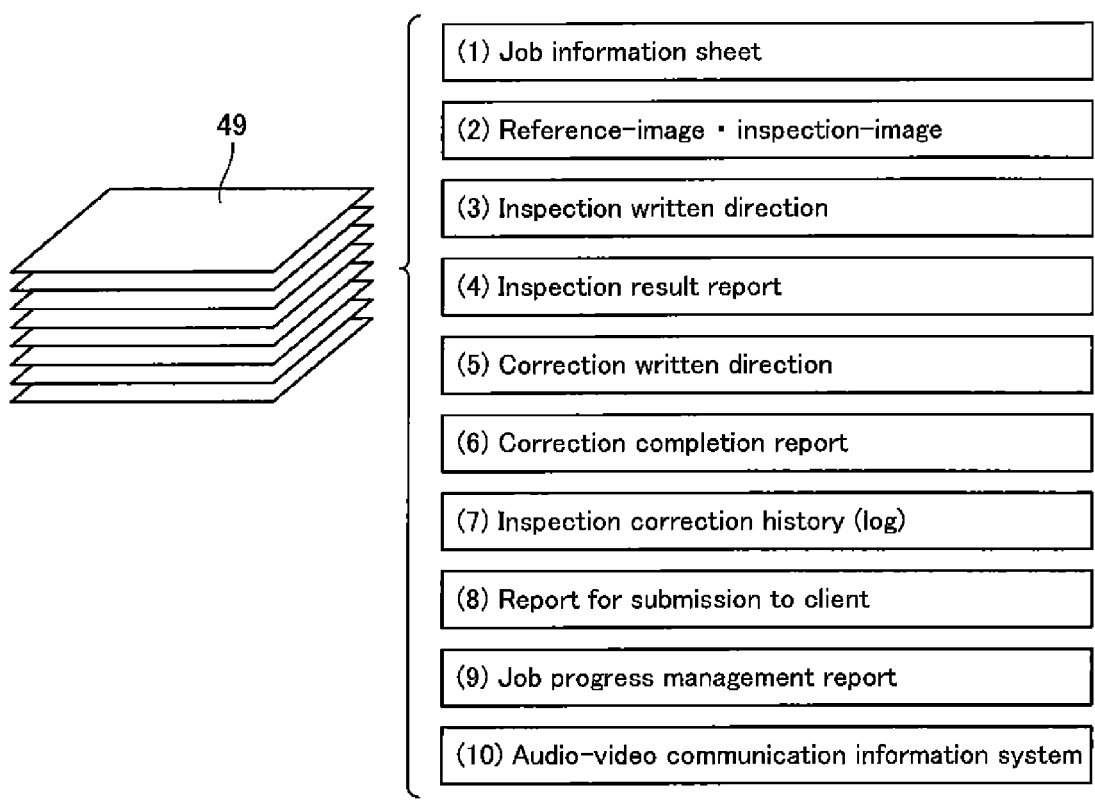
FIG. 12 is a block diagram illustrating a structure of an inspecting operation information sheet in an image inspecting apparatus according to a third embodiment of the present invention.
Figure 13:
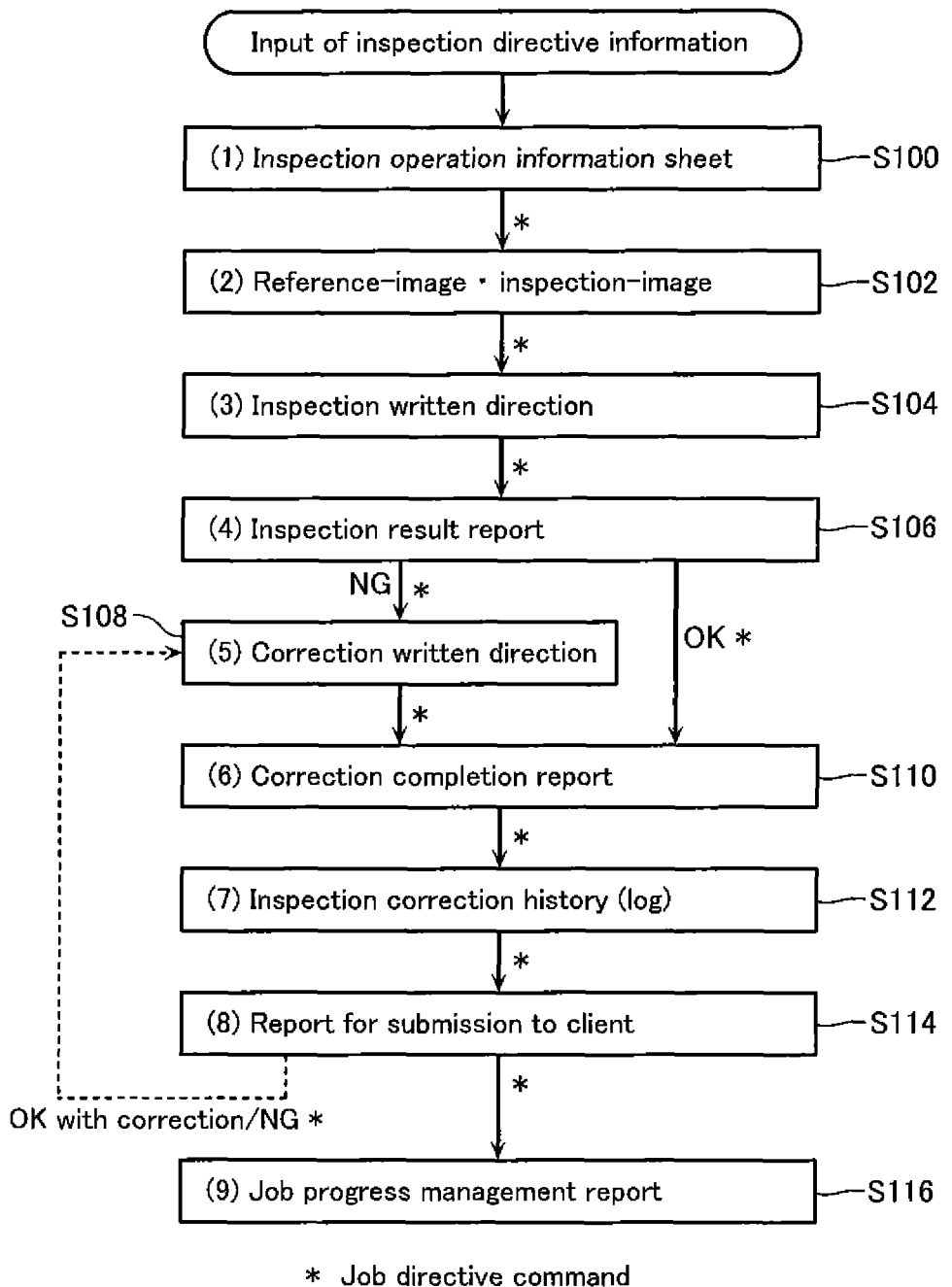
FIG. 13 is a flowchart illustrating the inspection flow of the inspecting operation information sheet shown in FIG. 12.
Figure 14:
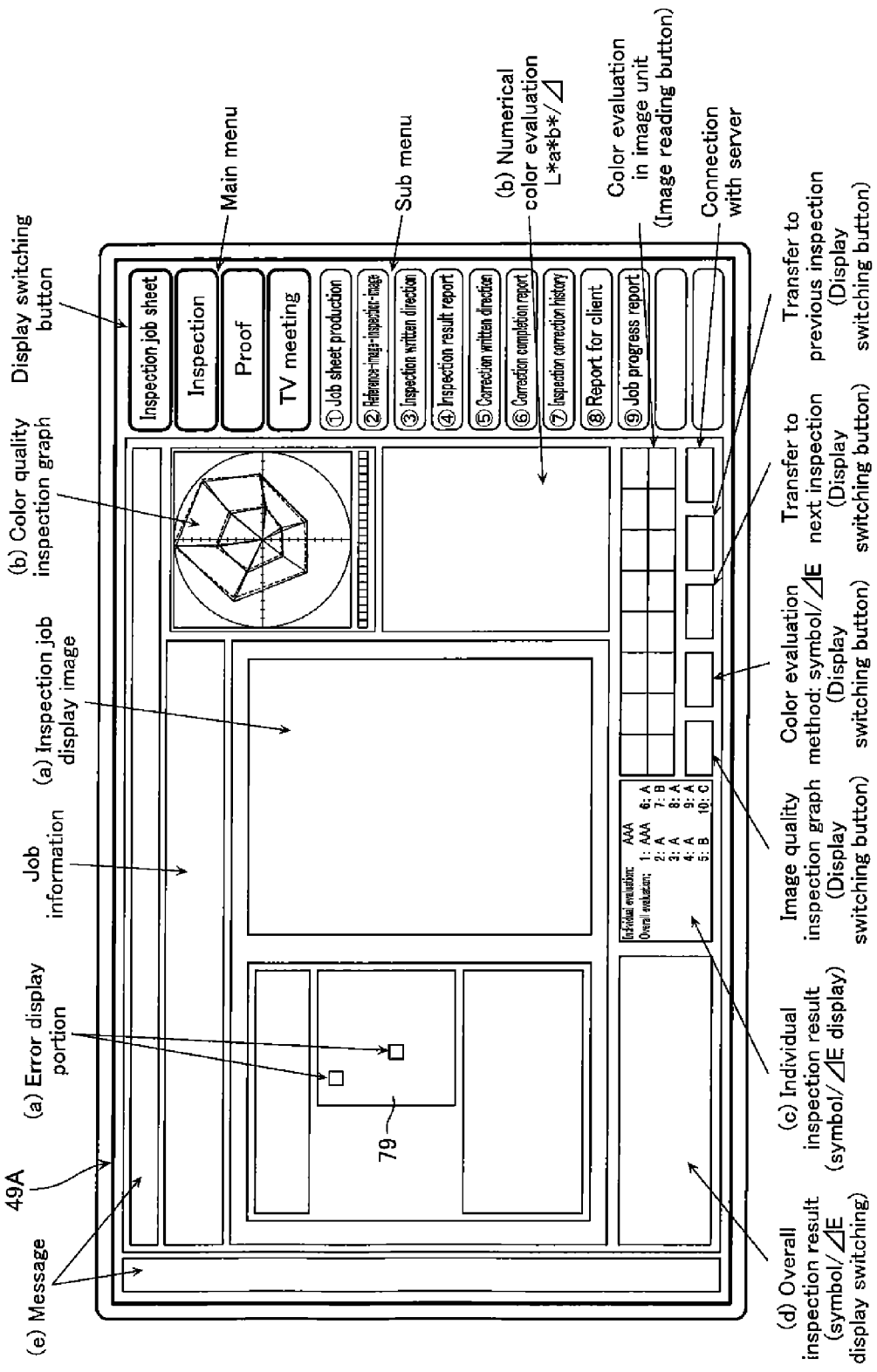
FIG. 14 is a diagram illustrating color evaluation image in the inspection result report of the inspecting operation information sheet shown in FIG. 12.
Figure 15:
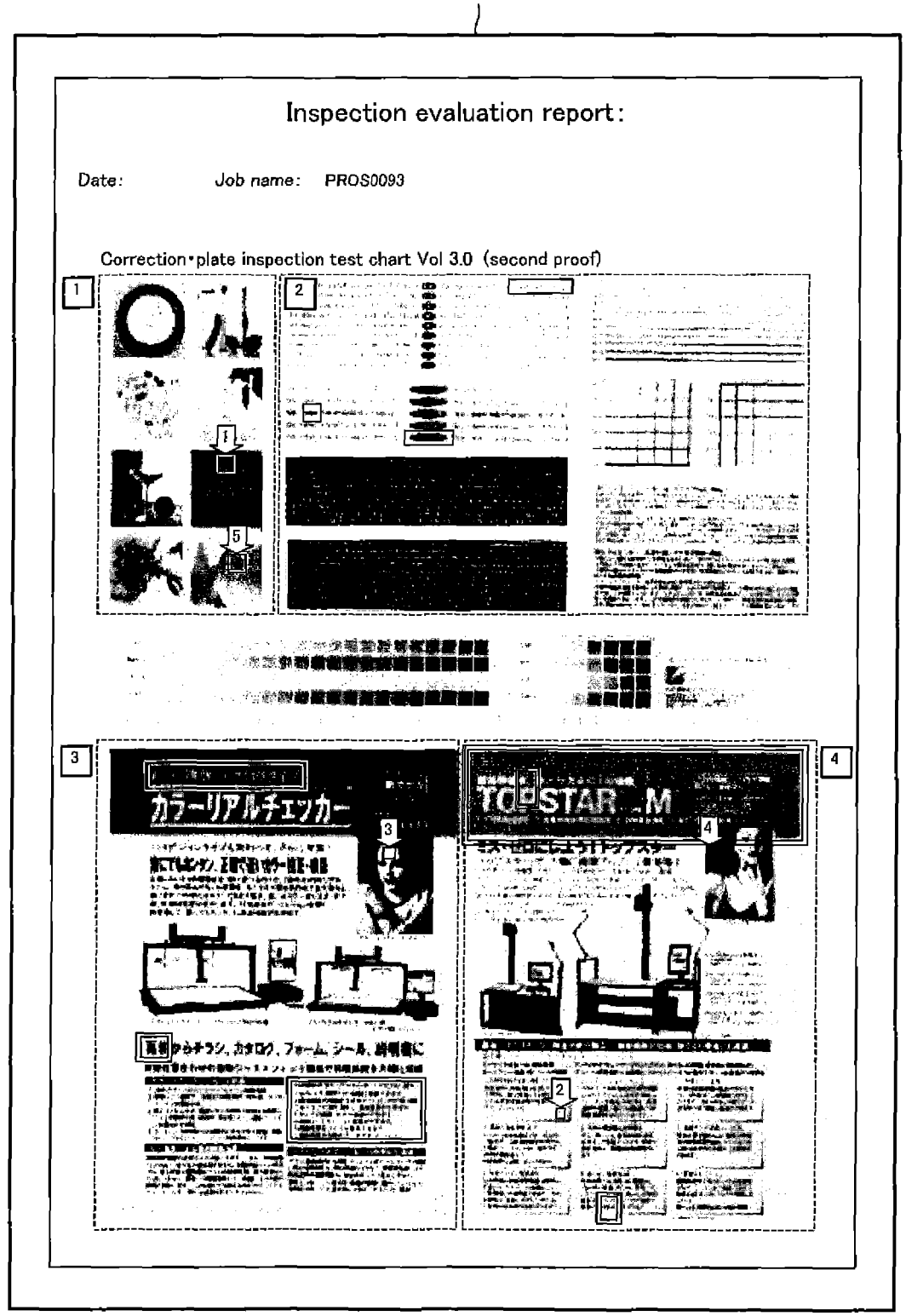
FIG. 15 is a diagram illustrating the back page of the inspection evaluation report in the inspection result report.

FIG. 12 shows a diagram explaining a structure of an inspection operation information sheet used in an image inspecting apparatus according to a third embodiment of the present invention. FIG. 13 is a flow chart of an inspection using the inspection operation information sheet. FIG. 14 is a diagram showing a color evaluation image in an inspection result report of the inspection operation information sheet. FIG. 15 is a diagram showing a back page of the inspection result report of the inspection operation information sheet. FIG. 16 is a diagram showing a front page of the inspection result report of the inspection operation information sheet. The image inspecting apparatus of the third embodiment can be implemented with the same structure and function as those of the image inspecting apparatuses 10 of the first and second embodiments. In this third embodiment, image inspection is performed based on the inspection operation information sheet 40 shown in FIG. 12. The inspection operation information sheet is an information electronic slip for instructing a printing operation to operators or instruments by means of commands, texts, image, video picture, and voice.

A Digital work flow using a network line is utilized in order to develop a rapid, precise and convenient printing work flow. For that purpose, it is necessary to realize reliable and effective business communication within the office and to clients in producing procedure of printed matter, and to realize a digital network flow for performing a quality control of every step, from proofreading of printed matter and so on to delivery inspection. Two this end, the digital inspection operation information sheet is used in each order entry job.

As shown in FIG. 12, the inspection operation information sheet 49 is composed of (1) a job information sheet, (2) reference-image-inspection-image, (3) an inspection written direction, (4) an inspection result report, (5) a correction written direction, (6) a correction completion report, (7) an inspection correction history (log), (8) a report for submission to a client, (9) a job progress report, and (10) an audio-video communication information system. Further, the inspection operation information sheet 49 has (A) a slip function, (B) a progress information management function, (C) an inspection result displaying function, (D) a correction command function, and (E) a communication function. There will be described functions of the inspection operation information sheet 49.

The first function of the inspection operation information sheet 49 includes sending a first image data and second image data for inspection, which are input by an image input device and to which job direction commands are attached, from one PC or different PCs to one server for inspection by means of storage means for storing the reference-image and inspection-image. At an inspection site, at least a part of the first and second image data are called as the reference-image and the inspection-image from the server for inspection, in which the first and second image data are stored in the image inspecting apparatus, by job direction commands, and at least parts of the corresponding images are correlated and image-matched. Further, the matched first and second image data are compared to detect difference value between both the image data. In this case, the threshold value and the difference are compared to produce difference point display image data at the threshold value, and image inspection processing is performed using the produced difference point display image data.

The second function of the inspection operation information sheet 49 includes dividing the reference-image and the inspection-image before and after image matching of the input images, and inspecting at least a part of the reference-image and at least a part of the reference-image as the first and second image data at a plurality of threshold values, based on inspection directive information as job directive commands.

The third function of the inspection operation information sheet 49 includes generating inspection directive information as job directive commands, extracting and correlating the stored reference-image and inspection-image based on the job directive commands, and performing image matching of these correlated images as the first and second image data.

The fourth function of the inspection operation information sheet 49 includes producing or preparing information containing correction data necessary to designate PC and display on a monitor and correction directive commands, storing a server if necessary, or sending and displaying the information to PC of clients, based on correction job directive commands of the inspection operation information sheet 49.

The fifth function of the inspection operation information sheet 49 includes adding automatic control commands or manually corrected communication comment information for enabling to correct the correction display part of the inspected image based on inspection evaluation information of the image difference point inspection results, and (region) part of contents corresponding to the corrected parts based on job directive commands, by means of, for example, plug-in software of DPT application software, performing changing, removing and adding of a color, text, photograph, figure and so on, and automatically or manually correcting the positions.

The sixth function of the inspection operation information sheet 49 includes reconfirming whether or not the corrected image has been corrected according to the directive commands based on correction job directive commands of the inspection operation information sheet 49, and displaying the results.

The seventh function of the inspection operation information sheet 49 includes automatically preparing inspection results as an inspection result certificate in each job or in each designated inspection region based on job directive commands of the inspection operation information sheet 49. Mark "re-inspection" or "inspection" is attached to the inspection result certificate depending on the contents of inspection.

The eighth function of the inspection operation information sheet 49 includes generating log information such as a job name of image inspection processing by PC, an inspection site, an inspector, inspection contents, an inspection starting date, inspection finished date, and inspection finished time, sending them as inspection progress information to the inspection information server, and displaying them on each terminal device, based on job directive commands.

As described above, when a ganging image inspection is performed, a plurality of ganged job images are arranged as reference-images. In a plurality of inspection-images, the same job images are single-image paginated or step-and-repeat paginated in each job. For that reason, positional information in each single-image paginated or step-andrepeat composed image ganged as the inspection-image is obtained in individual job image used as the reference-image in the inspection operation information sheet 49, and commands are prepared in the inspection operation information sheet 49, based on this positional information. Alternatively, it is possible to automatically perform image matching and image inspection by linking the reference-image with inspection-image in all jobs. Further alternatively, if only there are performed direction of commands in the inspection operation information sheet 49, which includes designating image contents such as characters, pictures, and figures of the reference-image and the inspection-image in all the jobs, directing repeat number of the step-and-repeat paginated inspection-image, and command directing automatic searching, the reference-image is automatically linked to the inspection-image. Therefore, it may be possible to automatically perform image matching and image inspection of all the ganged reference-image and inspection-image. Further, it is possible to input directive information of all contents necessary for inspection such as inspection position and inspection accuracy into commands in the inspection operation information sheet 49.

A flow of the fundamental operations of inspection and correction shown in FIG. 13 using the inspection operation information sheet 49 thus constructed, is as follows:

(1) At first, job information and job directive commands are input to the inspection operation information sheet 49 (step S100). The input job information includes the job data from exclusive printing operation management system and management information system (MIS), and information which is necessary for the inspection operation information sheet 49 and is obtained by selecting inspection operation in PC screen from an electronic slip directing operations. The information to be obtained includes a name of a trader, client information (company name, name, division and post of a person in charge), information regarding a job of an order received (job name, date of order received, expected date of deliver, submit data for printing, submit matter for printing (color sample), finish size, number of ink color, number of printed set, kinds of paper, number of pages, surface treatment, folding method, binding method) and so on. Inspection operators select a name of an inspector and a job name of inspection.

Subsequently, an inspection date, an inspection position and an inspection operation step are selected, (2) the reference-image and the inspection-image are selected (step S102), (3) an inspection written direction are selected (step S104), and thereafter an inspection is actually performed. The selection of the reference-image and the inspection-image are performed by selecting a digital-input image of, for example, PDF or printed matter obtained using camera or scanner and storing it in the image file of the inspection operation information sheet 49. The inspection direction includes proof information from the office and clients.

The inspection written direction is provided with a layer specifying an inspection area for a product to be inspected or inspection digital data. The inspection area is linked to inspection directive commands based on job directive commands. Inspection directive comments are written in the inspection written direction together with the inspection directive commands. When the inspection is performed, the selected reference-image and inspection-image (2) are image-matched by means of comparative inspection software, and subsequently, the comparative inspection is performed based on the inspection directive commands for determining inspection accuracy, at the threshold value in which the inspection written direction (3) is written in the other layer. It is possible to automatically or manually designate inspection contents by means of the pointing device.

After inspection is performed thus, (4) the inspection result report is output (step S106). The inspection result report includes the inspection results which are separated from the other layer than that of the inspection-image and are displayed in a form boxed with a marking frame representing a difference value between the reference-image and the inspection-image. The inspection result report includes the inspection date, the inspection division, the inspector, the number of the inspection position specifying difference value detecting part and the inspection error part, the contents of the inspection position specifying difference value detecting part and the inspection error part, the inspection area, threshold value, and the inspection results, together with the inspection job information.

When the inspected image is rated as NG in the inspection result report, (5) a correction written direction is output (step S108). The correction written direction includes (a) a first proof correction direction and (b) a client proof correction-modification direction. If inspection error (rejection mark) is recorded in the inspection result report, characters or colors in the inspection part are confirmed according to an inspection directive column of the correction written direction of (3). If there is a faulty point, a correction position and correction contents (dot gain correction amount, correction amount due to tone correction method of pictures and dot % of each CMYK version, difference value of L*a*b*, color difference ΔE, and so on) are written in the other layer than that of the correction directive column of the inspection result report or the inspection-image by means of directive commands for text sentence and automatic correction. And then, the direction to CPU output of the prepress section of the previous step is automatically or manually performed.

DTP application software cooperating with the contents of the above-described correction direction and plug-in software separately developed are started to automatically or manually correct the inspection-image based on correction directive commands of the inspection operation information sheet 49. On the other hand, regarding the correction which cannot be automatically performed, manual correction is performed according to the contents of the correction directive text by means of the pointing device.

And then, the reference-image (2) before inspection and the inspection-image after automatic or manual correction are image-matched and comparative-inspected by means of the image inspecting apparatus. If the difference between both the images disappears, (6) a correction completion report is output (step S110). For example, if there is uncorrected portion in even a part of the image, the inspection-image is returned to step S108, in which it is automatically described and corrected.

At the time of correction, (7) an inspection correction history (log) is output (step S112). The inspection correction history describes when and which step the inspection and correction operations were performed, who and what times performed the inspection and correction operations, and whether finish operation or finish proofreading. These are automatically linked to the file of the inspection operation information sheet 49 or another storage file as a log based on job directive commands and are exported. (8) The report for submission to a client is output (step S114). The report for submission to a client is reflected from the partial information in the final inspection result report (4) and is sent to a client. When the report for submission to a client is rated as final proof/NG, it is described in the correction written direction (5), and a correction operation is restarted.

Lastly, the job progress management report (9) is output based on the job directive commands (step S116). A progress management table representing confirming the image folder for inspection, the first proof and the final proof in the inspection-image is automatically prepared by using the job progress management report. This information is transmitted to the progress management system and so on, and is used to confirm to what extent each job progresses in work schedule.

Further, when this information is transmitted to the progress management system or MIS, improvement in an operation effect in the design division, the prepress division, and the printing factory division can be visualized based on frequency of character correction, frequency of color correction, frequency of color adjustment, printing time, cost management, electric power, kinds of ink, reduction effect of carbon dioxide and so on. In final proof, difference point of images due to operation error and collections-modifications by a printing orderer after submitting a manuscript are categorized, costs are allotted between factory costs and business costs depending on causes of operation costs, and the obtained data are sent to MIS and so on.

There will now be described an important inspection directive method contained in the inspection operation information sheet 49, and a mechanism and effect of outputting various operation management reports from the inspection operation. Firstly, (3) inspection written direction is explained. The inspection direction in (3) inspection written direction includes recording an important item to be inspected such as characters, images and so on which are regarded as important by clients, and directing important points in the case in which operators automatically check the finish and confirm the inspection results and threshold values such as a level of an inspection accuracy and so on. Specifically, the following directions are performed.

The directions includes starting PC 11 and comparative inspection software, which are used in the image inspection system and the image inspecting apparatus 10, image-matching the first and second image data 31, 32, and performing comparative inspection in the inspection commands recorded in the layer different from that of the inspection-image, such as threshold values. It is possible to designate the inspection contents using the pointing device.

The inspection results are displayed on the back page 70 of the inspection evaluation report in the inspection result report (4), as shown in FIG. 15. More specifically, the inspection results are displayed in a form boxed with the marking frame 34 in the difference point display image of the inspection result difference point display image data 33 produced from the result of image matching and difference inspection of the first and second image data 31, 32. The difference in color is displayed in a form boxed with the frame 71 of different color. Incidentally, the inspection results may be displayed on the back page or page 2 of the inspection operation information sheet 49, or on page 2 of the inspection result report.

As shown in FIG. 16, the number of difference points of characters and colors inspected at the threshold value in each inspection region and the threshold values are recorded in the front page 72 of the inspection result report. Further, the difference points of colors are separately displayed as color difference ($\Delta E$) or tone difference obtained from L*a*b* profile-converted from RGB. Though the color tone means $\Delta a$ value and $\Delta b$ value obtained by removing L* value from L*a*b* value, term "tone difference" is used to distinguish from "color difference" These may be displayed on the front page or page 1 of the inspection operation information sheet 49, or page 1 of the inspection result report.

The inspection operation information sheet 49 is displayed is output on each page in the case of single page, and in paginated job unit in the case of paginated image. However, where the paginated job is divided into single pages and inspected, the inspection operation information sheet 49 is output (issued) in a single page unit or as a paginated page.

Next, the inspection result report (4) is explained. The inspection result report (4) includes the following information obtained after image inspection as shown in FIG. 14.

(Main Contents of the Inspection Result Report)
(a) Inspection job display image and error display part: Display images such as error and so on are shown.
(b) Color quality inspection chart and numerical color evaluation: Color quality inspection results are shown.
(c) Individual inspection result: The image inspection result in individual difference point display part is shown.
(d) Total inspection results: The total inspection results (determination of good or bad, average color difference, and so on) are shown.
(e) Message: The comments on the correction contents to the inspection results and correction method are shown.

In these image displays, various inspection-images are switched to an error display screen or message area screen by operation of the image inspecting apparatus 10.

As shown in FIG. 14, an inspection result report 49A is a part of the inspection operation information sheet 49, and it is possible to display the contents of the inspection operation information sheet 49A on the display screen of the display unit 12 as shown in FIG. 14, or also to output them for printing or output as data as shown in FIGS. 15 and 16. Further, it is possible to display them together with the reports representing various evaluations in the inspection results of the image inspecting apparatus 10. The inspection result report 49A is prepared automatically or by operation input of inspectors, for example, automatically based on the inspection directive data stored in HDD29 or previous inspection correction history data.

On the other hand, data or proofs during production of DTO have been confirmed with the naked eye since it is necessary to confirm whether or not the previous first proof, revised proof, or data such as color comprehensive layouts of clients or PDF from clients are corrected according to directions or not. In order to automate these operations using instrument inspection, it is necessary to use the inspection written direction (3) in which inspection part, contents, and inspection threshold values are recorded as inspection commands, in addition to batch processing functions for continuously processing input or file storage of a pair of the reference-image and the inspection-image, image matching, inspection, and reports.

Therefore, job name registration of the reference-image is performed such that odd number is given after job name, and job name registration of the inspection-image is performed such that even number is given to input manuscript or file name of data. Further, automatic continuous batch processing program is set beforehand, whereby pair images are automatically prepared and matched only with job name, page number, and file number regarding data input in the same folders, and thus all inspection operations are automatically performed based on the inspection written direction (3). Furthermore, the inspection results, to which file name (for example, reference-image is named A image, inspection-image is named B image) and number in order of inspection are added, are output for printing, and are stored as data.

That is, there are represented contents data showing information regarding inspection jobs in each inspection job, images such as difference point display images showing difference point display parts by means of marking frames and so on, a color quality inspection chart showing color quality inspection results, numerical color evaluation shown in terms of L*a*b* value and color difference ΔE value as regards the image inspection results, total inspection results showing the total results of image inspection results, individual inspection results showing the image inspection results in individual difference point display parts, and so on, in the prepared inspection operation information sheet 49. Also, various display switch bottoms, image reading bottom, connection directive bottom to a server of an information processing apparatus 110 described later or the above-mentioned audio-video communication information system (multimedia information system) (10) may be displayed on the display screen displaying the inspection result report 49A.

For example, it is displayed such that a directive mark on the directive layer representing correction parts overlap a marking given in the inspection whether correction parts are properly corrected or not, in DTP operation step. On the other hand, evaluation is easy since there is not marking, in the part in which correction is not performed. That is, where all corrections finish, the image is rated as OK, where there is an uncorrected part, the image is rated as NG, or the uncorrected part is displayed, and these are recorded in the inspection result report 49A.

Different points are detected from the difference point display of the image in which existence or nonexistence of dirt, contaminant, and flaw are inspected in the inspection of character region of the image. In this case, if total number of pixels in the difference point block in which pixels are connected is large, it is judged that both the characters are different. On the other hand, if there is a marking in the corrected part of the characters, finished correction is recorded in the report, and if not, NG is described in the report as error.

Difference of block as a linear shape of at most a few pixels or minimum dirt, which is fully visible on printed matter, has a size of a block consisting of 5 pixels in the case of an image of 200 dpi resolution. Even in the case of a block consisting of 5 pixels or more, for example, 20 pixels, the block having a low density as a whole is counted as dirt, and the amounts of the dirt are recorded in the report. The difference points such as a dirt, flaw, blur, stain and so on are designated in different marking colors, whereby correction operation can be easily performed.

In the inspection result report 49A, ΔE may be represented separately in stages using not only characters but also numerals (for example, 1.3, 2.0, 3.5, 4.0, 5.9) or evaluation marks (for example, AAA, AA, A, B, C, D). Further, a notation which is generally considered as easily understandable (for example, OK/NG, o/x) may be employed. Furthermore, a part of this report result may be used as (8) the report for submission to a client, as described above.

Finally, "the contents of printing job from bar code of MIS or a printing operation slip" and "the contents of printing direction from clients or quality controllers and correction direction from proofs" are reflected, and decision results determined by inspectors in charge are described. All or a part of the following information (a) to (g) is integrated in the inspection operation information sheet 49. Where OK is input as inspection results in the step, it is considered that the operations till the step has been completed.

Incidentally, even if the inspection results is OK, it is not considered that the operations of the steps has been completed till agreement of a printing orderer in charge or a responsible official is obtained finally. Therefore, the following information, in which an inspection finish and an operation finish are separated, may be preferably described in the inspection result report 49A.

(a) Inspector, inspection job, number of inspection (inspection No. 1, 2, 3, - - - n)
(b) Date, inspection position, inspection operation step, number of inspection, inspection threshold value, inspection printing face image
(c) Conventional inspection time, present inspection time
(d) Direction of correction part in each inspection region and decision of OK/NG
(e) Detection of typographical error and dirt and inspection of dirt amount
(f) Display of color frame boxing color evaluation (difference between tone difference ΔE and CMYK %) and color difference preset with numerals (value such as ΔE) in important color measuring part designated by clients.
(g) State of inspection results (OK/NG)

Next, (5) a correction written direction is explained. When the correction written direction (5) is represented in the individual inspection result representing column of the inspection result report 49A shown in FIG. 14 included in the inspection operation information sheet 49 shown in FIG. 12, error (difference point) such as a correction omitting part in the inspection and dirt and contamination of the inspection-image and the detected part are represented.

The correction written direction directs how the difference point displaying part in the difference point displaying image boxed in the marking frame should be corrected. It makes a person in charge in each division correct easily based on the inspection operation information sheet 49. The correction written direction may include correction commands which make CPU 21 of the image inspecting apparatus 10 automatically correct based on pertinent correction directions.

The part, in which a difference exceeding the threshold value set in the inspection result report 49A is detected, is represented by a marking frame and color. Regarding the part in which automatic determination of the difference is difficult, the inspector in charge determines whether characters in the correction part is properly corrected or not. If he determines OK, he requests approval confirmation in the marking frame. In this case, color coding may be performed with another color.

Further, where an authorized person is asked for the determination, it is necessary to construct such a mechanism that the inspection result report 49A is sent to the person directly or through a communication means such as voice-image communication information system or e-mail, and a feedback is received from the person. Regarding the part in which the direction of correcting color difference is confirmed, the measurement point and the measurement number are described on the image, and CMYK % is represented on the other screen. Also where the color difference is larger than previously determined difference, the color difference preset depending on the degree of the difference is represented in the display color which is easily visible at a glance.

The correction part found by a proof is designated by marking together with the image or on the other layer prepared separately from the image. The information including the correction part and the correction contents is overlapped by the display image like a transparent overlay, whereby the directive information can be read out. Hereby, it is possible to determine without fail whether the part to be corrected is properly corrected or not. In the case of the correction of characters, finally, the characters are visually confirmed. In order to quickly estimate the results of correction, a marking frame is selected on the layer to reflect OK or NG in the inspection result report 49A.

In DTP operation step, it is displayed such that the directive mark on the layer representing the correction part overlaps the marking of inspection whether correction is performed on the correction part or not. In the part in which correction is not performed, it is easy to estimate that since there is not marking of inspection. Further, since the correction contents of characters are represented in a balloon by clicking a marking, it is possible to determine at once whether a proper correction is performed or not. "OK" in the case where all corrections are completed and "NG" in the case where there is at least one uncorrected part are stored and recorded as the inspection result report 49A and progress management data, and displayer on the display screen of the display unit 12 as information representing progress management. And then, all the operation history is sent to PC and reflected as progress management data.

In the printing step, the final paginated data or OK sheets are compared with the printed matter taken out to record difference in images and number of difference points such as dirt or contaminant, which are generated in test printing, in the inspection result report 49A. The parts, in which difference values in image density or color tone are detected, are marked on the image 79 on the left side of FIG. 14, which corresponds to the contracted image of the printed matter, and recorded in the inspection result report 49A. The information is converted into correction directive information commands together with comments on the parts necessitating these corrections to obtain a correction written direction directing the next correction processing (5), whereby correction parts can be automatically displayed in close-up on a monitor screen.

The correction written direction may be one in which difference point display images such as JPEG, TIFF image and so on are converted into PDF, and are written. Hereby, confirmed/unconfirmed of directions such as proof, correction and so on can be performed by checking, circling or signing person's name in charge.

Various data included in the inspection operation information sheet 49 are stored in, for example, a server of an information processing apparatus in an image inspection system described later. The data are confirmed by an operator of a printing machine to utilize in color adjustment of the printing machine, or to construct direct interphase with the printing machine. Hereby, it is possible to directly control the ink key of the printing machine.

In this case, if an ink characteristic curve showing the relationship between a dial value representing an open-close degree of the ink key, which controls an amount of ink set in the printing machine, and picture area ratio of the printed matter is previously prepared, it is possible to calculate an ink correction amount more precisely.

The instruction of a color correction of the inspected image is performed by starting DTP application software or utilizing image correction function of RPI. In this case, it is performed by the following method while seeing the image displayed on the PC monitor of clients or the monitor of a mobile information terminal.

To designate correction amount of curve and halftone in numerical value (CMYK %) by tone curve correcting function To select an optimum image from images displayed in different brightness To directly correct by means of a color correction tool such as a dropper tool and so on To select an optimum image from various gray balance images Further, the correction operation is explained. DTP application software is started. When the correction operator confirms that corrected parts, correction numbers and a correction method are described in the inspection operation information sheet 49 by commands, and clicks the correction number by a pointing device and so on, the correction contents are displayed. And then, when the corrected part is designated using the software specially developed as a plug-in of correction application software, the DTP application software automatically performs a correction operation of colors and texts. After the correction operation is completed, application software for comparing the display data before and after correction in order to confirm correction is arranged.

Then, in order to easily visualize correction confirmation difference display, it is better to enable not only display of data difference, but also alternating display. The correction results are automatically added to server data together with a name of an operator and operation date information to the server data and stored.

Next, (6) a correction completion report is explained. Where errors are not found in the inspection result report 49A, difference points are not found when the inspection-image corrected according to the correction written direction (5) is inspected based on the information of the inspection written direction (3), or there are not errors in the inspection result report 49A, a correction completion report (6) is issued, and recorded in inspection correction history as a log.

And then, an inspection certificate, which certifies pass of inspection, is issued to clients. The inspection certificate is utilized also as a quality inspection certificate of first proof inspection, reproof inspection, nth-proof inspection, and receiving inspection of clients. Hereby, the clients can receive finished delivery goods with security. If further correction or modification is necessary, the goods are dealt as OK with correction or NG, and an additional correction is directed in the correction written direction (5).

Next, (9) a job progress management report is explained. The information described in the job progress management report (9), for confirming progress of operations in each step or job, such as an operator, a step, and completed steps, can be extracted from the information obtained through the above-mentioned operations. The information to be extracted relates to design production, DTP operation, RIP processing, proof output, OK proof/OK proof with correction in the proof operation for proof order of orderer, printing plate (CTP data) output, and printing operation.

Further, the job progress management report has a function of separately treating a progress management and cost management of operations in order to report working hours in each step in a job progress management. Where an operation written direction is read out by means of a bar code reader, or MIS is used before each of steps such as DTP operation or RIP processing, color adjustment of CTP output and printing, and printing run, an electronic operation written direction or JDF/JMF information is read out to record an operation start time. When PDF data is input in the image inspection system after operation, it is possible to automatically record the end of operation.

Further, in the prepress step, the inspector in charge inputs a proof image in the image inspection system as inspection data to inspect it, and gives approval to corrected parts and printing quality. At that time, the progress of operations is recorded. In the printing step, inspection of the printed image during color adjustment in the printing machine is started, and at the same time, measurement of color adjustment time in printing is started. And then, time for the color adjustment repeated several times till the color measurement of the last printed matter is measured.

Time from the last color measurement till finishing of the last sampling inspection of the printed matter is measured as a printing time. These measurement time and times of color measurements in color adjustment of the printing machine as times of color adjustments are measured, and are transmitted to an apparatus for performing progress management of operations or software of progress management.

The inspection history data are data showing contents of image inspection and stored in each inspection job, and includes an inspector in charge, date, and inspection position of image inspection in the image inspecting apparatus; image data such as the reference-image and inspection-image used in inspection; and a log of processing contents of the image inspection processing. The inspection history data can be also displayed on the display screen of the display 10 in the form of a graph and text.

Based on the above-mentioned information, inspection in each step is performed regarding a name of an operator, a step in which an operator operates, and a progress situation. These items to be inspected include design division performing DPT operation, prepress division performing RIP processing and proof output, orderer's signature of proof in each order-received job, OK proof with correction of printing company which is entrusted by an orderer with correction, a printing plate (CTP plate) output completion, and start-end of printing. As a result, operation progress information of each job is obtained, which is sent to process control software in real time. Hereby, it is possible to confirm a situation.

A printing method, a kind and size of paper, and a kind of ink of a previously received job, costs of these, and standard operation time in each inspection accuracy are input, and a report showing cost reduction effects are prepared based the above-mentioned operation progress information obtained by utilizing the image inspection system. The report is displayed on the screen of the display unit of the progress management system or the monitor screen of the mobile information terminal.

Further, it is possible to confirm whether production efficiency to an estimated operation time is good or bad, and the progress results have cost reduction effects to the estimated cost or not, at the time when the progress situation of each received job is confirmed, operations are finally completed, and the products are delivered. In this case, where operation commands for displaying the progress of inspection condition in each inspection operation on the monitor screen in real time, are input automatically or manually, it is possible to obtain data for confirming the progress of proof and inspection, production efficiency and cost reduction effects. Also the inspection result report 49A can be output in job unit.

Based on the inspection result report 49A, difference between an operation time and the standard operation time is analyzed from the progress steps and operation time obtained by inspection in each step to calculate the operation time. Based on the calculated operation time, the operation time spent in the job operation in each step is evaluated, and the operation contents, correction operation, and a difficulty level of the inspection contents and inspection accuracy are considered. It is evaluated in the present system that the inspection result report 49A is utilizable as a tool for confirming whether the received job enables sales profit appropriate to the job progress cost or not, the received job is effective or not, and the received job contributes to ECO effects such as material, electric power consumption and so on or not. The job effects can be realized by the following method.

That is, the total inspection results of the inspection result report 49A may include the following report columns. They include (a) paper cost reduction representing column and (b) waste paper reduction representing column as (A) paper reduction representing report. These columns (a) and (b) mainly represent reports regarding cost reduction. For example, "in the case of Kiku-series→A-series, Δ7.9% of paper cost of Kiku-series" is represented in column (a), and "paper reduction of 75 sheets per one printing×unit cost of @ 12 yen per one sheet in each kind of paper=Δ900 yen" is represented in column (b).

(B) Quality requirement classification report includes column (c) representing necessary time for ink adjustment target depending on quality requirement degree (in each ΔE value). Target necessary time, for example, "ΔE 1.0=90 minute, ΔE 2.0=45 minute, ΔE 3.0=35 minute, ΔE 4.0=30 minute, ΔE 5.0=25 minute, ΔE 6.0=20 minute" is described in column (c).

(C) Time reduction effect report includes column (d) representing operation time reduction and column (e) representing over time reduction. These columns (d) and (e) represent reduction of time and cost conversion. For example, "Δ50 yen/minute" is described in column (d), and for example, "Δ62.5 yen/minute" is described in column (e).

(D) Electric power reduction effect report includes column (f) representing electric power reduction. For example, "electric power W of machine, etc., electric power W of lighting+electric power W of air conditioner (distribution of the position)" is described in column (f). (E) Environmental effect report includes column (g) representing $CO_2$ reduction and column (h) representing usage rate of plant ink. Column (g) shows a report regarding $CO_2$ reduction amount depending on electric power reduction. Column (h) describes, for example, "–% (plant ink amount/total ink amount×100) used ink amount×number of sheets printed", and "plant ink=(1) soy ink, (2) - - - general oily ink=(11) 4 colors set, (12) characteristic, (13) - - - ".

Finally, (F) total evaluation report includes column (i) representing total evaluation per one day. Column (i) represents a report regarding a total evaluation of image inspection, and describes, for example, evaluation scale such as above-mentioned "AAA, AA, A, B, C, D, E, F, G, H" and evaluation point according to the evaluation scale, such as "10, 7, 4, 2, 1, −1, −2, −4, −7, −10". The total evaluation report includes column (j) representing quality degree+ estimated operation time according to printing number, which described sample-printing adjustment time in offset printing, gravure printing and flexographic printing, and estimated printing time in sheet-fed printing, rotary offset printing, business form printing, and label printing.

Above-mentioned information is written in the inspection operation information sheet 49 as progress management information, whereby a progress management of operations and efficiency of factory management can be realized. The information is sent to interoffice operation management system or MIS as data, and the aggregated data can be utilized for improvement in management.

[Fourth Embodiment]

Figure 17:
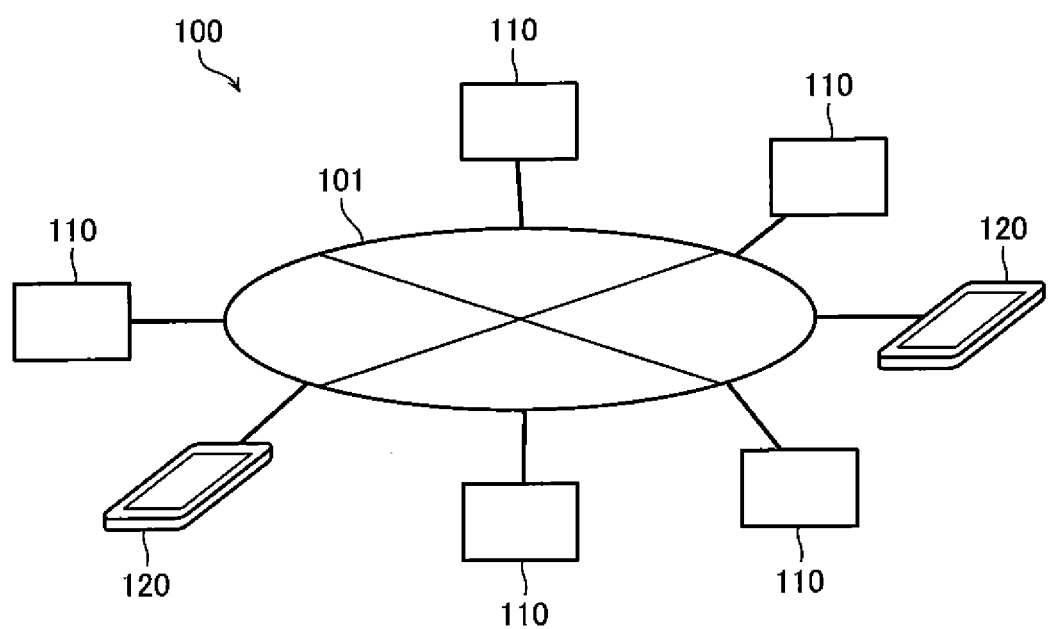
FIG. 17 is a diagram illustrating an image inspecting system according to a fourth embodiment of the present invention.
Figure 18:
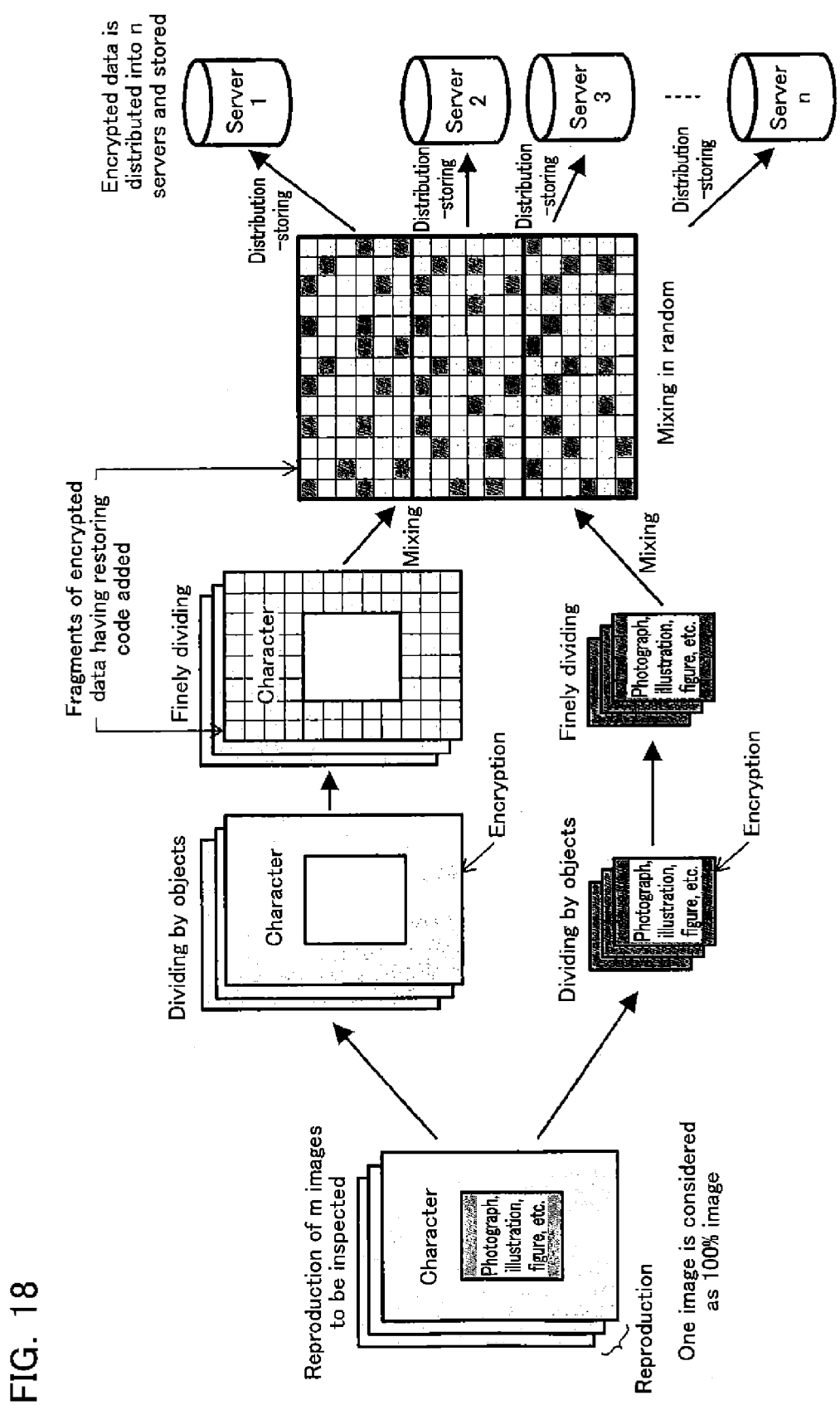
FIG. 18 is a diagram illustrating encryption and distribution storage of image data and so on in the image inspecting system.
Figure 19:
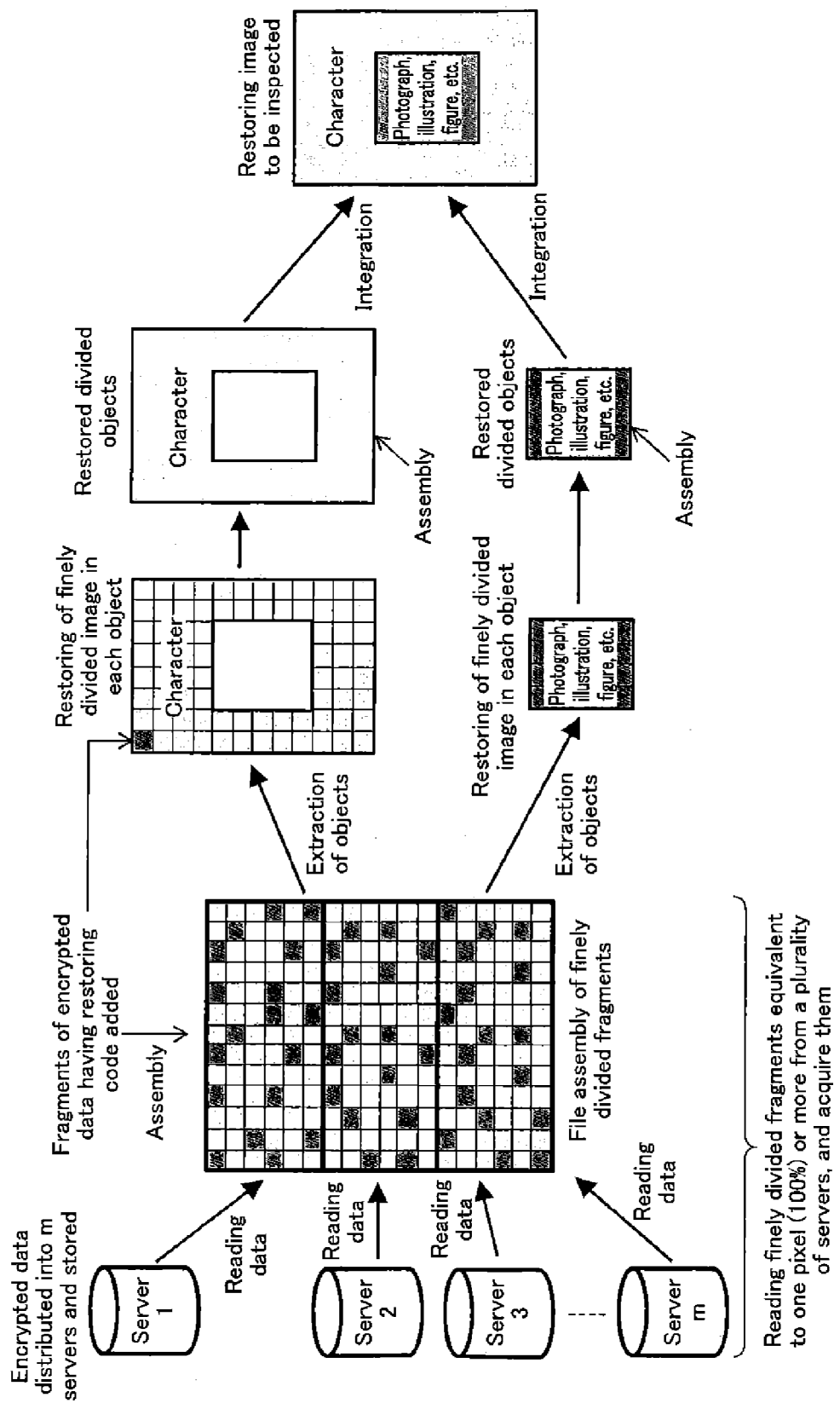
FIG. 19 is a diagram illustrating restoration of the encrypted and distribution stored image data to be inspected in the image inspecting system.
Figure 20:
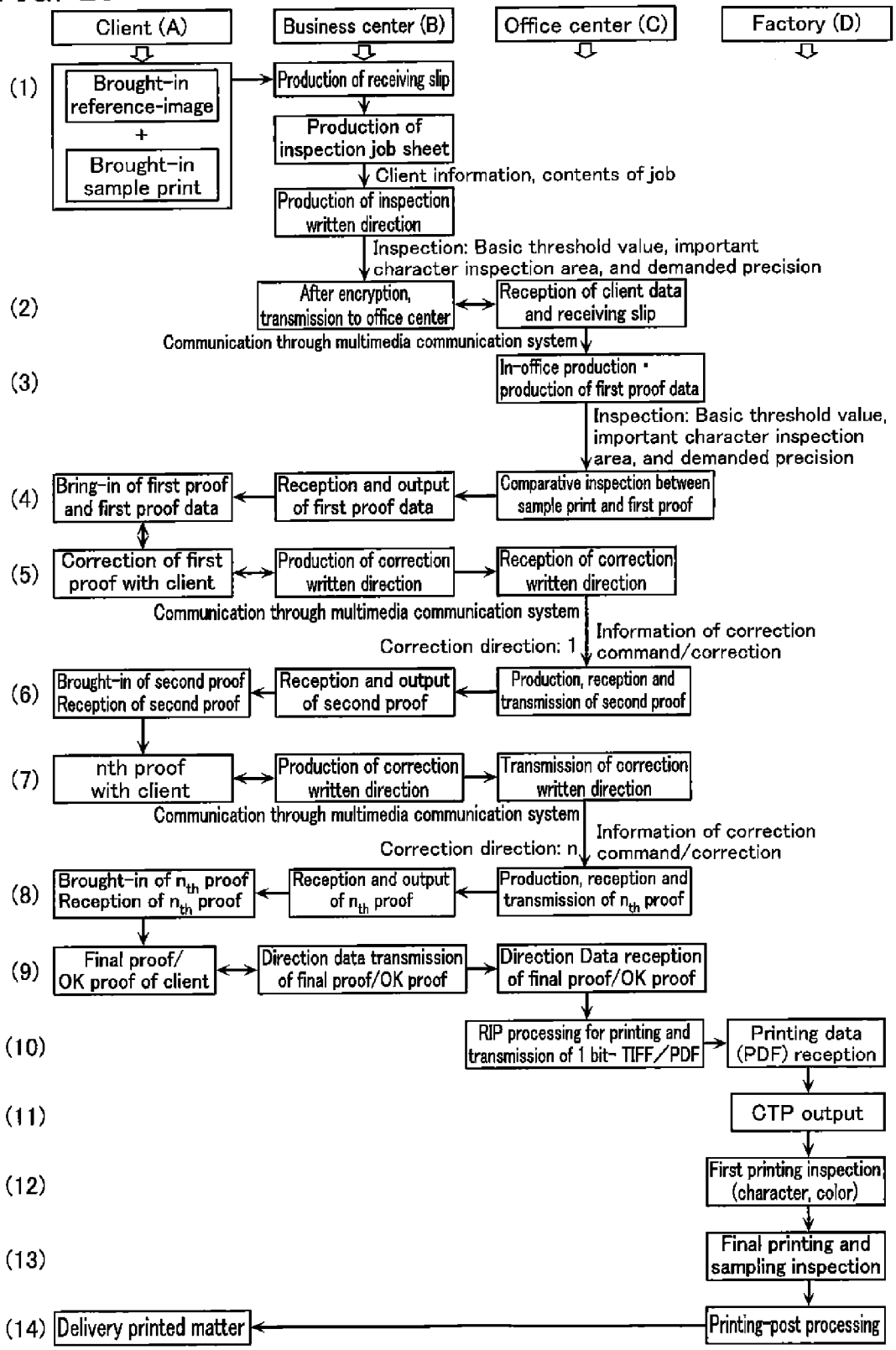
FIG. 20 is a flowchart illustrating the printing work flow in the image inspecting system.

FIG. 17 shows an image inspection system according to a fourth embodiment of the present invention. FIG. 18 is a diagram showing an encryption and distribution storage of image data to be inspected in the image inspection system. FIG. 19 is a diagram showing restore of encrypted and distribution-stored image data in the image inspection system. FIG. 20 is a flow chart of printing work flow in the image inspection system. In the image inspection system 100 according to the fourth embodiment, a plurality of information processing apparatus 110 including a personal computer and a work station is inter-communicably connected with a plurality of mobile information terminals 120 such as mobile phone, smart phone, notebook computer, tablet terminal and so on through a network 101. Incidentally, the information processing apparatus 110 and mobile information terminals 120 are provided with a telephone (telephone function) and image-sending and receiving function as voice-image communication information system, thus constructing a multimedia communication system.

Each information processing apparatus 110 is provided with the above-mentioned image inspecting apparatus 10. For example, at least one of the information processing apparatus 110 has a function as a server, and the other information processing apparatus 110 and the mobile information terminals 120 have a function as clients. According to thus constructed image inspection system 100, it is possible to confirm image inspection results of the reference-image and the inspection-image utilizing the above-mentioned multimedia communication system in the various information processing apparatus 110 and mobile information terminals 120 which are arranged at different locations such as a central office of a printing company, a printing factory, a business office, or clients.

As described above, in order to construct a printing work flow which is faster, more precise, and convenient, it is necessary to realize a digital network flow for performing consistent quality control from proof of printed matter till inspection of delivered matter by means of a safe information communicating means which makes the best use of a network line. For this purpose, the digital inspection operation information sheet 49 is utilized in each received job.

The ninth function of the inspection operation information sheet 49 includes sending and receiving safely image data for inspection and the inspection operation information sheet 49 (if necessary, refer to "image data for inspection, etc.") through a network using job directive commands of the inspection operation information sheet 49. The data for sending and receiving include a description language such as text data before and after inspection, hypertext markup language (HTML) data, extensible markup language (XML) data and so on; document data including image data such as a picture and illustration, or inspection-image data, and so on.

In order to safely send and receive the image data for inspection, etc., as shown in FIGS. 18 and 19, each of document data or each of images for inspecting image data for inspection are replicated to form replicas of the number which is sufficient for maintaining safety of restored information, are divided into rows of characters, photographs and figures, and are encrypted. Further, when data such as the image data for inspection are finely divided, restoring tag for restoring the finely divided data is attached to a piece of the divided data using random numbers, and stored in a single server or distribution-stored in a plurality of servers. In order to increase security, it is desirable to increase number n of servers than the number m of replicas not to restore data by means of information from one server. The document data or the image data for inspection may not be divided into rows of characters, photographs and figures. The images may be encrypted before or after replication of images or before or after division of data. Further, when public key and secret key are used, the secret key must be sent to the opposite party separately.

In receiving side, the divided and encrypted document data or image data for inspection received from the server are restored in each image to be inspected or in the block by means of the restoring tag using random numbers, are decrypted, and are managed as document data or image data for inspection. The server used herein refers to individual server or cloud type server. Where data are stored in freely combined servers, it is possible to deal with failure of a server or external information attack such as cyber terrorism for data protection. Replication, encryption, finely dividing, restoring code attaching using random numbers, and distribution storing are automatically directed in one process by previously setting directions of program operation. The reverse operations including calling of stored file, restoring of divided data, and decryption using random numbers of secret code are also automatically performed in one process.

As an example, at least two images to be inspected are divided into individual raw of characters, photograph, and figure, the divided or undivided images are encrypted, the encrypted images are finely divided into matrix form, and restoring codes using random numbers are attached to all pieces of finely divided images having data size of 1 KB. And then, the finely divided images are sent to necessary server or client PC in the block or separately.

In receiving side, the plural finely divided files in which individual image corresponding to inspection is stored, are called from the single or plural server or client PC, the finely divided piece images are integrated into one aggregated finely divided file. The piece images of the aggregated finely divided file are restored by means of restoring code using random numbers, and the encrypted data are decrypted to visualize one image to be inspected. Hereby, it is possible to distribution-store the image data for inspection and to perform safe information management by means of an information communication means.

The tenth function of the inspection operation information sheet 49 includes sending and receiving the reference-image, the inspection-image, the inspected difference point data and difference point correction commands, and easily performing communication for report, intercommunication and conference of difference points, by means of communicating means in interoffice correction check and client's correction check. That is, the fundamental function includes communication of image with voice, data communication of image to be inspected, communication of inspection commands, log information of inspection situation and so on. The inspection report is performed by means of multimedia communication. As described above, in order to avoid information leaks, it is better to provide a system which includes dividing the image to be inspected into regions of characters, photographs and figures, performing the other encryption of the divided unit, sending them to necessary server or client PC, and decrypting and restoring them. The related information of the inspection operation information sheet 49 is handled in the same manner.

By way of example, the first and second image data 31, 32 prepared by inputting images to the image inspecting apparatus 10 of the information processing apparatus 110 at a certain position and the inspection operation information sheet 49 are sent to the other image inspecting apparatus 10 of the other information processing apparatus 110 at another certain position by means of the network 101. The sent first and second image data 31, 32 are subjected to image inspection processing in the other image inspecting apparatus 10 of the other information processing apparatus 110. The inspection operation information sheet 49 including these image data 31, 32 and data regarding inspection results are sent to the information processing apparatus 110 having a server function at the further other position.

The information processing apparatus 110, which received the inspection operation information sheet 49 including an access code regarding the sent inspection results and the inspection result data, shares freely and accessibly the inspection operation information sheet 49 such as data regarding inspection results with the other information processing apparatus 110 and mobile information terminal 120 by means of multimedia communication system. Since the multimedia communication system has a function of mutually sending and receiving data such as telephone, image, e-mail, inspection proof, correction directive commands and so on, it is possible to transmit minute communication between a sending terminal and a receiving terminal.

If various information units thus connected with each other by means of the network 101 are utilized singly or integrally, it is possible to correct printing data using the inspection operation information sheet 49 including data regarding correction results and proof (correction) direction sent from the information processing apparatus 110 at remote locations through the network 101, to perform image inspection and re-inspection, to report the inspection results to the other information processing apparatus 110, and to mutually communicate through image or voice while keeping the log. Hereby, it is also possible to avoid transmission errors and easily confirm correction information, progress information, production efficiency, and cost reduction effects.

Where at least two images to be comparative-inspected and the inspection results are stored in the information processing apparatus 110 which is a server, it is possible to access and re-inspect the images from anywhere by means of the network 101. For example, where a standard proof image in the central office of a printing company is digitalized and stored as DB, the inspector transfers the images input or inspected in the image inspecting apparatus 10 in the information processing apparatus 110 of the printing faculty throughput the country to an inspection viewer. Where the images of the printed matter input in the information processing apparatus 110 of each printing factory are individually image-matched in the image inspecting apparatus 10, and defective portions are inspected. Hereby, it is possible to uniform a level of difference point detection in which threshold value of each factory is considered, and to inspect based on unified standard. Further, it possible to send data regarding the inspection results to clients and to access for clients to the information processing apparatus 110 provided with server function from clients.

Since the data searching functions using storing data of the first inspection job, a correction date of files, client name, job name, text, and thumbnails are added to the inspection operation information sheet 49, data management in each client can be handled in real time. Hereby, it is possible to improve efficiency of data preparatory operation and to provide information necessary for communicating with clients regarding directions such as a layout and correction of characters and images at once. As a result, both sides can effectively continue work.

In the image inspection system 100, in order to utilize a scheduler function such as process management software and MIS and to monitor the printing results at once, number of differences and correction from the image inspecting apparatus 10 and number of completed portions of check point in the corrected portion are counted to report-output or send them in on-line through the network 101. Hereby, it is ensured that confirmation of corrected portions between the information processing apparatuses 110 and the delivery of job to the next step.

Further, since the image color of the image inspection results during printing or after printing is confirmed as numerical value of difference in the color management section or business section in the image inspecting apparatus 100, it is possible to reduce the frequency when clients go to the printing factory at a remote location for attendance at the printing operation. Hereby, it is possible to improve operation efficiency of printing and to reduce printing costs.

However, in this case, it is most desirable to employ an image input device which can digitize images in L*a*b* value at high accuracy using a CIEXYZ filter, not RGB filter as a filter of a camera or scanner. Further, it is desirable that a standard deviation $\Delta E$ is 0.1 or less. In addition, it is important to perform precisely color management of a monitor, display unit, and proofer.

One reference-image used in comparative inspection and an image to be inspected are automatically searched and selected from the images stored in the information processing apparatus 110 having a server function through the network 101 to obtain the inspection-image. In the case of desk top publishing (DTP) data of the printed matter which has been printed for years and revised a number of times, when old image is called by mistake (regression), it is incidentally recorded in database as last utilized one. In this case, when automatic searching is performed, final page data are not called, and an erroneously corrected image is regressed. Then, if it is displayed in the event of search at any time whether related approximate images or page data exist or not, mistake of regression can be avoided. In the case of modification or correction of image files, it is desirable that the image inspection system 100 is provided with a search engine which stores and displays a series of correction history, and arranges a surely necessary final image or page data.

Where a data base server (DB server) is constructed in the information processing apparatus 110 of the central office of a printing company, password is given to clients (orderer), and a DB region for the exclusive use of clients is provided in folder unit, it is possible to safely separate the DB server from that of the other client and utilize it. Further, codes for the exclusive use of clients are added to file names of all data from the submission stage of a manuscript, a mechanism which prevents from erroneously transferring data to the other client is designed, and processing such as encryption, duplication, fine dividing, and distribution-storing of image data for inspection described above or later are provided, it is possible to perform a DB management having a highly security function.

However, where data are erroneously sent, it is necessary to taken measures to avoid information leakage to the third parties who access the data. The measures include sending encrypted data and handing over a decoding code or password directly to client or responsible division, which enable to confirming safety of data communication.

That is, where the reference-image and inspection-image to be comparatively inspected or corrected information and corrected image of clients are utilized in the network 101, it is necessary to (a) avoid information leak or store the images. Further, it is necessary to (b) construct such system that even if PC, a storage device of a mobile information terminal or a server of a cloud fail, data can be restored at once. In order to realize the functions (a) and (b), for example, the above-mentioned methods can be adopted.

All the data needed by parties concerned such as documents, images, direction slip and so on, to be accessed or sent in the network 101, are encrypted, finely divided in such a manner that they are perfectly reversible, duplicated such that even if there are failures of information devices or cyber attack, the data can be restored by the other information devices, and distribution-restored in confidence in a plurality of storage devices.

For example, even if one portion or a plurality of portions of PC or HDD fails, data are restored from a plurality of HDD storing many duplicated image data for inspection. Since, even if information drains outward, finely divided data cannot be restored, it is not information leakage. In this case, restoring codes are attached to all pieces of finely divided images in matrix for restoring. Further, even if the data can be restored, they cannot be decrypted without decryption key of the encrypted information. The functions of these series of operations may be added to the inspection written direction of the inspection operation information sheet 49. The fine division system of data is widely utilized in general information managements.

There will now be explained specific operations of the image inspection system 100, taking application to printing company as an example with reference to FIG. 20. In FIG. 20, an alphabetic letter in parenthesis denotes classification of each concerned division. (A), (B), (C), and (D) denote a client, a business center, a central office, and a factory, respectively. A numeral in parenthesis of (1) to (14) denotes a step. Accordingly, a combination of an alphabetic letter in parenthesis and a numeral in parenthesis or only numeral in parenthesis denotes a step of process flow.

At first, a client brings the reference-image and a sample print to a business center of a business office and so on (1-A). Based on these, the business center prepares a receiving slip, an inspection operation information sheet 49 including client information and job contents, and an inspection written direction for directing a reference threshold value for inspection, inspection areas of important characters, photographs, figures and needed precision (1-B). The business center encrypts the prepared matter and sent them to the business management division of the central office from a business base (2-B). The business management division encrypts the receiving slip sent from a certain business office, the color sample print data from the client, and the image data or PDF data which are the original data of the color sample print data, sends them to the central office (2-c), and request a design division to design based on these data and DTP operation (3-C).

The design division performs designing and DTP operation based on received PDF data, corrects and produces various images with reference to the color sample print data, prepares DTP data in which layout such as a text is designed, and requests a prepress division to prepare a first proof data together with the DTP data. The prepress division conducts RIP processing of the DTP data based on layout-typesetting composition, prepares, for example, 8-bit correction print data necessary for color inspection and proof PDF data in addition to 1 bit image data, and comparative-inspect with the sample print. In the inspection, the prepress division sets a reference threshold value for determining fundamental inspection accuracy and needed precision to the inspection area using the inspection written direction from the business office, so as to perform the inspection meeting the client's demands.

In the stage of the first proof, a person in charge in the business office print-outputs proof papers by a printer using correction print data sent from the prepress division of the central office, by means of the image inspecting apparatus 10 of the information processing apparatus 110 (4-B). Next, the person in charge in the business office brings the proof PDF data encrypted in the mobile information terminal 120 and the output proof papers to the client (4-A), decrypts the proof PDF data using the client key, and gets the decrypted proof PDF data proofed by the client.

In the proof by the client (5-A), the client proofs directly the proof PDF data of the mobile information terminal 120 using the multimedia communication system. While the client confirms whether corrections are performed according to directions or not, if there is a faulty point still, the client marks directly the layer of the inspected image in a certain color, encrypts the data, connects the mobile information terminal 120 with the network 101, and sends the encrypted data to the deign division of the central office or the certain server through the multimedia communication system (5-C).

In this case, since the data encrypted in the image inspection system are sent through the multimedia communication system, it is possible to safely transmit the detailed data. For example, the encrypted image representing the printed matter which is corrected by the client and directed by the business office (printed matter image) is displayed on the monitor screen of the multimedia communication system. The image representing the printed matter and the corrected portions are numbered, and the numbered corrected contents are stored in the manner of texts and voice files. When the number on the image is clicked, the texts and voice files are displayed and reproduced. It is possible to be in communication with field operators by means of TV telephone using a voice and an image.

Next, in the re-proof stage, the design division of the central office (6-C) decrypts the encrypted image from the person in charge in the business office (5-B) based on the data sent from the mobile information terminal 120 through the multimedia communication system by means of the network 101, corrects the corrected portions of the fundamental design image mutually or automatically using the correction directive text of texts and colors or correction commands, preparing the corrected DTP data, encrypts them, and request the prepress division (6-C) to inspect them.

The prepress division (6-C) decrypts the encrypted DTP data, conducts RIP processing of the decrypted DTP data, image-matches the corrected re-proofed data converted into PDF data and the image data before correction, compares and confirms automatically or manually using the correction commands of the correction directive report. The prepress division puts an inspection stamp on the right and upper portion of the inspected image, encrypts it, sends the encrypted image to PC or the mobile information terminal 120 of each business office or the person in charge (6-B) through the multimedia communication system, sends the encrypted file of the inspection result report including the difference point display image data which is inspection results capable of perspective-displaying on the screen of the display unit 12 in the image inspecting apparatus 10 of the information processing apparatus 110, and enables the re-proofed papers to be printed by the printer 19.

The business office (6-B) confirms the corrected portions based on the re-proof data using the image inspecting apparatus 10 or mobile information terminal 120 of the information processing apparatus 110. The person in charge of the business office outputs the confirmed data based on the re-proof data and the data regarding the inspection results, encrypts the data, sends the encrypted data from the information processing apparatus 110 or mobile information terminal 120 through the network 101 to the information processing apparatus 110 or mobile information terminal 120 of the client (6-A) by means of the multimedia communication system, bring them together with re-proof papers to the client (7-A), decrypts the encrypted re-proofed image, gets the decrypted re-proofed image proofed by the client, and sends the re-proofed data to the design division of the central office (7-C).

Where the multimedia communication system is utilized using the mobile information terminal 120, the processed inspection result data at each threshold value, critical threshold value, and confirmed results are encrypted in the condition where the inspection result image is marking-represented in advance using the information processing apparatus 110, and the encrypted data are sent to the business office or client, whereby the inspection results are safely and precisely confirmed. If more precise inspection is desired (for example, an agate or two-dimensional bar code), it is possible to perform a re-inspection by displaying the marking information of the inspection results when the threshold value is changed to that higher than the threshold value set in the information processing apparatus 110 on the display screen of the information processing apparatus 110.

And then, in tri-proof operation step, the above-described operations are repeated till OK proof or OK proof with correction, these operation history data are automatically stored in HDD 29 of the information processing apparatus 110 having a server function such that it is utilized as business management data, OK proof or OK proof with correction data are encrypted, and the encrypted data are sent to the prepress division of the central office.

The prepress division (10-C) decrypts the sent printing data, conducts RIP processing of the decrypted data, sends encrypted image data of, for example, 1 bit TIFF or PDF data thereof to the printing factory (10-D). The printing factory (11-D) decrypts the received image data of 1 bit TIFF or PDF data, uses the printing plate output from CTP recorder, inspects color difference between the printed sample and OK proof/OK proof with correction, character missing, dirt, and flaws in the adjustment of a printing ink by the printer (12-D), and starts printing (14-D) when inspection errors disappear. Where a sampling inspection (13-D) is performed during printing, it is possible to prepare reliable printed matter without full inspection. After printing (14-D) is over, processing and so on is performed, and delivery of the printed matter to the client (14-A) is completed.

Figure 21:
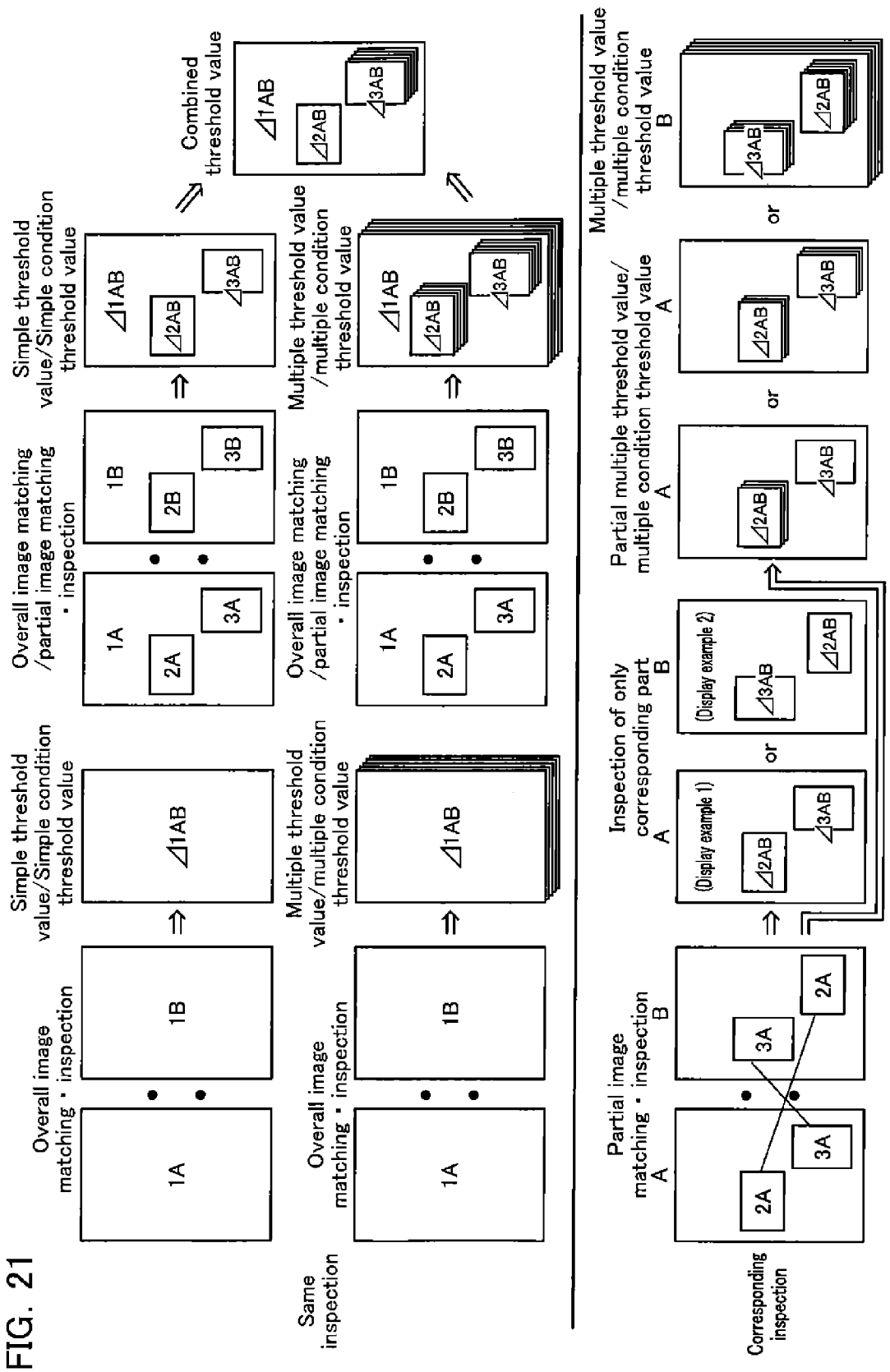
FIG. 21 is a diagram illustrating the inspection configuration in the image inspecting system.

As explained above, according to the image inspecting apparatus, image inspecting program, and image inspection system of the embodiments, it is possible to perform image inspection of the reference-image and the inspection-image by data processing constructed safely at a low price. According to the image inspecting apparatus, image inspecting program, and image inspection system of the present invention, it is possible to realize a rough inspection conformation of the image inspection as shown in FIG. 21.

As described above, "simple threshold value" is different from "condition threshold value" in that "simple threshold value" is used in the case where an inspection value is set in one threshold value and one inspection result is obtained, and "condition threshold value" is used in the case where an inspection condition is set in a combination of at least two threshold values and one inspection result is obtained. The cases shown in FIG. 19 are applied to both "simple threshold value" and "condition threshold value". Incidentally, "simple threshold value" includes one "single threshold value" which is set as one inspection threshold value in order to obtain one inspection result, and "multiple threshold values" which is set as a plurality of inspection threshold values in order to obtain a plurality of inspection results. Further, "condition threshold value" includes "single condition threshold value" which is set as at least two inspection threshold values in order to obtain one inspection result, and "multiple condition threshold values" which is set as a plurality of inspection threshold values in order to obtain a plurality of inspection results.

That is, in the same inspections, where an image 1A as a first image data and an image 1B as a second image data are image-matched in the entire region/partial region and a comparative inspection is performed at a single threshold value or a single condition threshold value, one difference image $\Delta$1AB can be obtained. Where a comparative inspection is performed at multiple threshold values or multiple condition threshold values, a plurality of difference images $\Delta$1AB can be obtained. $\Delta$ denotes a difference.

Where an image 1A including partial region images 2A, 3A and an image 1B including partial region images 2B, 3B are image-matched in the entire region/partial region and a comparative inspection is performed on each partial regions in different threshold values or a single condition threshold value, difference images $\Delta$2AB, $\Delta$3AB can be obtained together with a difference image $\Delta$1AB. Where a comparative inspection is performed in multiple threshold values or multiple condition threshold values, a plurality of difference images $\Delta$1AB, $\Delta$2AB, $\Delta$3AB can be obtained. Further, where these are combined, the entire regions are compared in multiple threshold values or multiple condition threshold values, it is possible to obtain a difference image $\Delta$1AB. Where the partial regions are compared at a single threshold value, it is possible to obtain a difference image $\Delta$2AB. Where parts of the partial regions are compared at multiple threshold values, it is possible to obtain a plurality of difference images $\Delta$3AB. Thus, it is possible to perform image inspections in combined threshold values.

In a corresponding inspection, for example, where partial region images 2A, 3A, which are different in layout and correspond to each other in images A, B, are image-matched and comparatively inspected, for example, in display example 1, a difference image $\Delta$2AB is obtained in the partial region of the partial region image 2A in the image A, and a difference image $\Delta$3AB is obtained in the partial region of the partial region image 3A. For example, in display example 2, a difference image $\Delta$3AB is obtained in the partial region of the partial region image 3B in the image B, and a difference image $\Delta$2AB is obtained in the partial region of the partial region image 2B.

Where the multiple condition threshold value is applied to the partial region image 2A, which is a part of the image A, a plurality of difference images $\Delta$2AB are obtained. Where the other single condition threshold value is applied to the partial region image 3A, a difference image $\Delta$3AB is obtained. Where the multiple condition threshold value is applied to the partial region image 3A, a plurality of difference images $\Delta$3AB can be also obtained.

Further, for example, the multiple condition threshold value is applied to the partial region images 3A, 2A, and all the other partial region images to obtain a plurality of difference images B, Δ3AB, Δ2AB, which may be image-inspected. Thus, according to the present invention, even if parts of the image B to be inspected move and are interchanged in arrangement position, the entire region and parts are separately image-matched and inspected, whereby the results of the comparative inspection can be displayed in various display styles.

The comparative-inspection program used in PC 11 of the image inspecting apparatus 10 explained with reference to the above-described embodiments can be realized by being executed using various computers. The comparative-inspection program are recorded in various recording medium such as HD, DVD, Blu-ray (registered trademark) disc, memory card and so on, which can be read by a computer device, read out by a computer device, and distributed through transmitting medium such as an internet.

Since printed matter is utilized also as a product package, it is necessary to inspect a plane printed image as the reference-image and a printed image attached or thermally bonded to a three-dimensional product as the inspection-image. In order to realize this inspection, the printed surface of the three-dimensional product is image-input by means of a line scan camera and so on to obtain a plane inspection-image, and this inspection-image and the plane printed image as the reference-image are image-matched and comparative-inspected. Alternatively, the plane printed image is image-mapped corresponding to the image data of the three-dimensional product to be comparative-inspected to prepare the reference-image, and this reference-image and the three-dimensional inspection-image are image-matched in each face region unit of three-dimension, and comparative-inspected.

Where a three-dimensional image is converted to a two-dimensional image and this two-dimensional image is comparative-inspected, it is important to select an image matching reference point for image matching. Therefore, the two-dimensional image obtained by inputting a three-dimensional product using the above-described line scanning camera is divided into profile lines or deformation-adjust to subject to mapping based on the profile lines or images which are divided so as to be easily image-matched with the image developed to a plain as a two-dimensional image of a partial region in each shape face. Hereby, it is possible to comparative-inspect with the image obtained by taking the photograph of the three-dimensional product.

Conversely, a three-dimensional image of a three-dimensional product to be comparative-inspected with a two-dimensional image is divided into regions which is easily subjected to mapping, image-matched in each partial region, and inspected. Further, in this case, the two-dimensional image may be mapped to a CAD image based on CAD information of the product. The coordinate representing shapes of various three-dimensional products is stored as CAD information, and image mapping is performed using the information as reference-image data of three-dimensional products having the same shape.

For example, printing on a can, a PET bottle and so on is performed on a plane paper, a plastic film and so on by means of gravure printing, flexographic printing, or offset printing. For example, printed matter printed on a plane medium is attached to a three-dimensional product to form a finished product. In this case, where the printed surface of the printed matter attached to the product is inspected, the plane printed matter is often the reference-image, and the printed matter attached to the three-dimensional product is often the inspection-image.

Therefore, where printed matter is attached to a three-dimensional product, or a three-dimensional product is directly printed and molded, a test chart for correction of distortion is necessary. In this case, in order to allow inspection even if the plane figure on a three-dimensional product changes, a test chart for correction of distorted 3D image to which matrix lines are added, is printed on the same member as the product to be inspected.

At this time, the test chart for correction of distorted 3D image is image-input by a line scanner, area scan camera and so on, and correction processing of the distorted 3D image is performed so that the plane image of the test chart for correction of distorted 3D image and the three-dimensional input image can be image-matched. And then, the plane image is replaced with the three-dimensional image, or the three-dimensional image is replaced with the plane image using a correction processing of distorted image program, these images are distortion-corrected to the images having corresponding shapes, and the images having the same parts are subjected to position adjustment and inspection.

In this case, matrix lines are previously added to the test chart for correction of distorted 3D image, and the correction processing of distorted image is performed using the matrix image of black and white as the table chart of correction of distorted image. And, the images are comparative-inspected using the image conversion data of this distortion table. Incidentally, the above-mentioned image input is performed using indirect illumination such as flat and uniform skylight.

In an automatic inspection for a medical diagnostic imaging, there are various imaging apparatuses for diagnostic imaging (Modality), so-called picture archiving and communication system (PACS) such as CT, MRI, X-ray and so on. There will be described a management system in which an image input by PACS is computerized and stored in a database, and the image can be perused.

In medical facilities, higher medical instruments such as computed tomography (CT) and magnetic resonance imaging (MRI) are in wide-spread use in each medical center. These medical instruments provide an important information source utilized by medical doctors in diagnosis and operation using imaging.

In the diagnosis imaging using such an automatic inspection apparatus, since several dozen of tomogram images in each inspection are necessary, medical doctors, who must view all tomogram images, occasionally overlook. Therefore, it is demands to develop a system which provides data regarding the inspection results obtained from comparative inspections of the tomogram images and enables medical doctors to diagnose exactly and quickly.

Where the image inspection system 100 is utilized for medical purposes, it is required to extract focus images from images of inspection subjects and to represent information necessary for diagnosis of doctors such as a position of a focus, a kind of a focus, inspection facility, inspector, inspection date and so on, together with images and diagnosis support information.

Further, all information including medical information concerned and diagnosis results, which are stored in computers and can be utilized for diagnosis, is managed in system. The information is displayed on a display screen of PC of a medical doctor, and corrected based on a patient's file for diagnosis, tomogram image, three-dimensional processing image, and support information and so on. On the tomogram image display screen, moving pictures and still pictures are continuously displayed, and slice information of each tomogram image is continuously displayed on the display screen of PC in order. Further, it is better that the display screen of PC is provided with a communication function by means of text or voice, a storing function, or a medical case inquiry searching function. Medical doctors make a comprehensive diagnosis based on an original image of a subject, auxiliary information provided from an information support system, and a patient's file.

A navigation system for brain surgery is explained. The system consists of an image input section, an image matching section, an image analysis section, and an image diagnosis navigation support section. The image input section prepares a three-dimensional model image based on a two-dimensional image of CT or MRI, and image-matches images in each of the same regions of a subject. The image analysis section analyzes, makes a comparative-diagnosis, and prepares image diagnosis navigation support information.

That is, the image analysis section provides fundamental information such as a figure and position of each region texture of a subject, inspection facility, an inspector, an inspection date and so on, and common information such as anatomic name and importance obtained by referring database to the image diagnosis navigation support section. The image diagnosis navigation support section displays a three-dimensional image based on a two-dimensional image, sets a route from a body site to an affected part using display software such as stereoscopic vision and a graphic user interface (GUI), and displays the image inspection and diagnosis information based on information from the image analysis section and database.

User interface (UI) for system operation includes an operation menu, a three-dimensional display screen, and a one way display screen. The operation menu includes a selection of a display image, a selection of a display method, and so on. The three-dimensional display screen includes an adjustment mechanism for a color display, extension, contraction, rotation of an affected part on a navigation support screen.

Each person in charge and so on (medical doctors and full-time medical experts) displays mainly this image information on the display screen of PC and observes the affected part. In addition, he provides the observer positional information of whole body using a position sensor technique. Further, it is better to integrate a real space in which each medical doctor exists with a virtual space in which patient's data in computer exist, and show as if he observes the affected part or around of the real patient and operates the affected part Where images are managed and stored as image data, it is possible to reduce a storage location of silver films and effectively utilize the empty space. Storage, search, and carrying-out of silver films can be reduced by digitalization and this contributes to reduction of time and cost. Further, it is possible to avoid loss of silver films. In addition, it is possible to add information such as lines, arrow indication, comments to the fundamental information, and store it as image data if necessary. Hereby, it is possible to easily search inspection data one wants from various information regarding patients and inspections.

REFERENCE SIGNS LIST

10: Image inspecting apparatus
11: Computer main unit (PC)
12: Display unit
13: Mouse
14: Key board
15: Pointing device
16: Camera
17: Scanner
18: Work table
19: Printer
20: Bus
21: CPU
22: Main memory
23: Image control section
24: Data input section
25: Operation input section
26: Data output section
27: Communication module
28: Image memory
29: Hard disc drive (HDD)
30A: Reference medium
30B: Inspection medium
31: First image data
32: Second image data
33: Inspection result error display image data
34: Marking frame

The invention claimed is:

1. An image inspecting apparatus for comparing first image data created as data representing a reference-image acting as an inspecting reference with second image data created as data representing an inspection-image acting as a target to automatically extract a difference point between the first image data and the second image data, comprising:
   a storage means for storing the reference-image and the inspection-image;
   an image processing means for establishing correspondences between at least a part of the stored reference-image as the first image data with at least a part of the stored target image as the second image data at a pixel level to perform an image matching processing of them;
   a difference detecting means for comparing the image-matched first and second image data to detect a difference between the first and second image data;
   an image producing means for comparing the difference with a plurality of threshold values to produce a plurality of image data, each of the image data including a plurality of pixels defining a single image, and each of the images being defined by each threshold value comparison to represent the difference point; and
   an image inspecting means for performing an image inspecting process using the image data to represent the difference point image data at each threshold value, and
   the image data to represent the difference point being stored in the storage means for using in the image inspecting process.

2. The image inspecting apparatus according to claim 1, wherein the image processing means performs an image dividing process for dividing the reference-image and the inspection-image stored in the storage means into a plurality of region images before or after the image matching processing, each of the region images being used hereafter as a process unit, which is the first and second image data.

3. The image inspecting apparatus according to claim 1, wherein the image processing means extracts the corresponding partial images of the reference-image and the inspection-image stored in the storage means, correlates them, and performing the image matching processing of the correlated partial images as the first and second image data.

4. The image inspecting apparatus according to claim 1, wherein the image processing means adapts one of the first or second image data to the other of the first or second image data using an image correction function when the image matching processing of the first and second image data is performed.

5. The image inspecting apparatus according to claim 1, wherein the first and second image data include image densities and color tones, and the difference detecting means compares separately the image densities and the color tones of the first and second image data to detect the differences.

6. The image inspecting apparatus according to claim 1, wherein the image inspecting means determines a critical threshold value based on the compared results between the threshold values and the differences, and produces the image data to represent the difference point.

7. The image inspecting apparatus according to claim 1, wherein the image inspecting means produces the difference point representing the image data based on the compared results between the difference point representing image data at different threshold values.

8. The image inspecting apparatus according to claim 1, wherein the image inspecting means switch-displays a plurality of the image data to represent the difference points such that the difference points representing portions are visible in different display manners for every image data to represent the difference point.

9. The image inspecting apparatus according to claim 1, wherein the first and second image data include color tones, and regarding the color tones of the first and second image data, the difference detecting means converts CIEXYZ image or RGB image into L*a*b* values and thereafter converts L*a*b* values into color differences $\Delta E$ or CMYK.

10. An image inspecting process for comparing first image data created as data representing a reference-image acting as an inspecting reference with second image data created as data representing an inspection-image acting as a target to automatically detect a difference point between the first image data and the second image data, comprising:
   a storing step for storing the reference-image and the inspection-image in a storage means;
   an image processing step for establishing correspondences between at least a part of the stored reference-image as the first image data with at least a part of the stored target image as the second image data at a pixel level to perform an image matching processing of them;
   a difference detecting step for comparing the image-matched first and second image data to detect a difference between the first and second image data;
   an image producing step for comparing the difference with a plurality of threshold values to produce a plurality of image data, each of the image data including a plurality of pixels defining a single image, and each of the images being defined by each threshold value comparison to represent the difference point; and
   an image inspecting step for performing an image inspecting process using the image data to represent the difference point, and
   the image data to represent the difference point being stored in the storage means for using in the image inspecting step.

11. The image inspecting process according to claim 10, wherein the image processing step performs an image dividing process for dividing the reference-image and the inspection-image stored in the storage means into a plurality of region images before or after the image matching processing, each of the region images being used hereafter as a process unit, which is the first and second image data.

12. The image inspecting process according to claim 10, wherein the image processing step extracts the corresponding partial images of the reference-image and the inspection-image stored in the storage means, correlates them, and performing the image matching processing of the correlated partial images as the first and second image data.

13. The image inspecting process according to claim 10, wherein the image processing step adapts one of the first or second image data to the other of the first or second image data using an image correction function when the image matching processing of the first and second image data is performed.

14. The image inspecting process according to claim 10, wherein the first and second image data include image densities and color tones and the difference detecting step compares separately the image densities and the color tones of the first and second image data to detect the differences.

15. The image inspecting process according to claim 10, wherein the image inspecting step determines a critical threshold value based on the compared results between the threshold values and the differences, and produces image data to represent the difference point.

16. The image inspecting process according to claim 10, wherein the image inspecting step produces the image data to represent the difference point based on the compared results between the image data to represent the difference point at different threshold values.

17. The image inspecting process according to claim 10, wherein the image inspecting step switch-displays a plurality of the image data to represent the difference points such that the difference points representing portions are visible in different display manners for every image data to represent the difference point.

18. The image inspecting process according to claim 10, wherein the threshold value includes a simple threshold value for evaluating in a condition of single threshold value and a multiple threshold value for evaluating in a condition of a plurality of threshold values.

19. The image inspecting apparatus according to claim 1, wherein the image inspecting process is performed based on an inspecting operation information sheet including the reference-image and the inspection-image, the inspecting operation information sheet adds job direction commands to the first image data and the second image data, the storage means stores the job direction commands together with the reference-image and the inspection-image, and the image processing means, the difference detecting means, image producing means and the image inspecting means perform each process respectively, based on the job direction commands.

20. The image inspecting apparatus according to claim 1, wherein the image inspecting process is performed based on an inspecting operation information sheet including the reference-image and the inspection-image, the inspecting operation information sheet adds job direction commands to the first image data and the second image data, the storage means stores the job direction commands together with the reference-image and the inspection-image, and the image inspecting means includes an image correction directive means for automatically or manually correcting difference point representing portions of the inspection-image relative to the reference image, which is displayed by the image data to represent the difference point, based on the job direction commands.

21. The image inspecting apparatus according to claim 1, wherein the image inspecting process is performed based on an inspecting operation information sheet including the reference-image and the inspection-image, the inspecting operation information sheet adds job direction commands to the first image data and the second image data, the storage means stores the job direction commands together with the reference-image and the inspection-image, and the image inspecting means sends inspection progress information indicating progress of the image inspecting process in each job to an inspection information server, thereby to enable to display the inspection progress information on each terminal device.

22. The image inspecting apparatus according to claim 1, wherein the image inspecting process is performed based on an inspecting operation information sheet including the reference-image and the inspection-image, and the inspecting operation information sheet directs sending and receiving of multimedia information including image and voice indicating the difference point representing portions displayed by the image data to represent the difference points of the inspection-image, inspection commands, an access code regarding the inspection results and the inspection result data.

23. The image inspecting apparatus according to claim 1, wherein a plurality of the image data to represent the difference points are stored in the storage means for using at least one of switching display and color separation display of each threshold value.

\* \* \* \* \*